US012648694B2

(12) United States Patent
Tsukihara et al.

(10) Patent No.: US 12,648,694 B2
(45) Date of Patent: Jun. 9, 2026

(54) OPHTHALMOLOGIC APPARATUS AND CAMERA DEVICE

(71) Applicant: TOPCON CORPORATION, Tokyo (JP)

(72) Inventors: Kouichi Tsukihara, Tokyo (JP); Satoshi Yamamoto, Tokyo (JP); Akira Takahashi, Tokyo (JP)

(73) Assignee: TOPCON CORPORATION, Tokyo (JP)

( * ) Notice: Subject to any disclaimer, the term of this patent is extended or adjusted under 35 U.S.C. 154(b) by 460 days.

(21) Appl. No.: 18/304,062

(22) Filed: Apr. 20, 2023

(65) Prior Publication Data

US 2023/0337914 A1      Oct. 26, 2023

(30) Foreign Application Priority Data

Apr. 21, 2022      (JP) .................................. 2022-070319

(51) Int. Cl.
 *A61B 3/14* (2006.01)
(52) U.S. Cl.
 CPC ....................................... *A61B 3/14* (2013.01)
(58) Field of Classification Search
 CPC ........... A61B 3/14; A61B 3/0008; A61B 3/12; A61B 3/0083; A61B 3/135; G02B 21/0012; G02B 21/06; G02B 21/362
 USPC ........................................................ 351/206
 See application file for complete search history.

(56) References Cited

U.S. PATENT DOCUMENTS

| 9,282,889 | B2 * | 3/2016 | Shikaumi | ............... | A61B 3/145 |
| 12,268,446 | B2 | 4/2025 | Nitta | | |
| 2003/0184711 | A1 * | 10/2003 | Abe | ........................ | A61B 3/135 |
| | | | | | 351/214 |
| 2004/0004695 | A1 * | 1/2004 | Sugino | ................... | A61B 3/145 |
| | | | | | 600/476 |
| 2006/0146283 | A1 * | 7/2006 | Baumann | ............... | A61B 3/113 |
| | | | | | 351/208 |

(Continued)

FOREIGN PATENT DOCUMENTS

| CN | 108769325 A | 11/2018 |
| CN | 114375175 A | 4/2022 |

(Continued)

OTHER PUBLICATIONS

Extended European Search Report mailed Sep. 8, 2023 in connection with European Patent Application No. 23168399.6, 7 pgs.

(Continued)

*Primary Examiner* — Mohammed A Hasan
(74) *Attorney, Agent, or Firm* — Chiesa Shahinian & Giantomasi PC

(57) ABSTRACT

An ophthalmologic apparatus includes an illumination system that is supported to be rotatable about a subject's eye with an irradiation direction of illumination light kept toward the subject's eye and an observation system that has a camera device and is arranged opposite to a position of the subject's eye across the illumination system. The camera device includes an imaging unit that receives reflection of the illumination light from the subject's eye and a light emitting unit for background illumination that is provided in the observation system and located below the subject's eye.

16 Claims, 15 Drawing Sheets

(56) References Cited

U.S. PATENT DOCUMENTS

| | | | | |
|---|---|---|---|---|
| 2011/0051085 A1* | 3/2011 | Kishida | .................... | A61B 3/12 |
| | | | | 351/246 |
| 2014/0111766 A1* | 4/2014 | Umekawa | ................ | A61B 3/12 |
| | | | | 351/205 |
| 2019/0298168 A1* | 10/2019 | Tatara | .................. | A61B 3/1035 |

FOREIGN PATENT DOCUMENTS

| | | | | |
|---|---|---|---|---|
| JP | 2002102173 | A | | 4/2002 |
| JP | 2004290461 | A | * | 10/2004 |
| JP | 20040290461 | A | | 10/2004 |
| JP | 2011078021 | A | | 4/2011 |
| JP | 2019170636 | A | | 10/2019 |
| JP | 2020-141998 | A | | 9/2020 |
| JP | 2020141999 | A | * | 9/2020 |
| JP | 20200141999 | A | | 9/2020 |

OTHER PUBLICATIONS

Notice of Reasons for Refusal mailed Nov. 4, 2025, in connection with Japanese Patent Application No. 2022-070319, 8 pgs. (including translation).

Office Action mailed Feb. 4, 2026 in connection with Chinese Patent Application No. 202310423610.1, 15 pgs. (including translation).

* cited by examiner

OPHTHALMOLOGIC APPARATUS AND CAMERA DEVICE

CROSS-REFERENCE TO RELATED APPLICATIONS

This application claims the benefit of priority under 35 U.S.C. 119 to Japanese Patent Application No. 2022-070319, filed Apr. 21, 2022; the disclosure of which is incorporated herein by reference in its entirety.

FIELD

The present disclosure relates to an ophthalmologic apparatus and a camera device which have a background illumination function and an imaging function for a subject's eye.

BACKGROUND

An ophthalmologic apparatus such as a slit lamp microscope having a light source as a background illuminator and a camera device has been proposed. The background illuminator is used to check the position of slit light applied to a subject's eye for observation of the subject's eye or to prevent a whiteout when capturing an image of the subject's eye with a camera. Japanese Unexamined Patent Publication No. 2020-141998, which is related to one of such apparatuses including the background illuminator and the camera device, discloses an ophthalmologic apparatus (a slit lamp microscope) having a background illuminator provided above an observation system and a camera device provided on the side of the apparatus opposite to the subject, i.e., closer to an examiner.

SUMMARY

The ophthalmologic apparatus of Japanese Unexamined Patent Publication No. 2020-141998 irradiates the subject's eye with illumination light projected from above. Thus, an observation region of the subject's eye may be shaded depending on the shape or state of an eyelid, for example. Further, the background illuminator requires a cable for connection with a power source separately from a cable for connection between the ophthalmologic apparatus and the power source, increasing space for installing the ophthalmologic apparatus.

An object of the present disclosure is to provide an ophthalmologic apparatus and a camera device which have a background illumination function and an imaging function for a subject's eye in a simple configuration.

To achieve the above-described object, an ophthalmologic apparatus of the present disclosure includes: an illumination system that is supported to be rotatable about a subject's eye with an irradiation direction of illumination light kept toward a subject's eye; and an observation system that has a camera device and is arranged opposite to a position of the subject's eye across the illumination system, wherein the camera device includes an imaging unit that receives reflection of the illumination light from the subject's eye and a light emitting unit for background illumination that is provided in the observation system and located below the subject's eye.

To achieve the above-described object, a camera device of the present disclosure is configured to be attachable to an observation system of an ophthalmologic apparatus including an illumination system that is supported to be rotatable about a subject's eye with an irradiation direction of illumination light kept toward a subject's eye and the observation system that is arranged opposite to a position of the subject's eye across the illumination system, wherein the camera device includes an imaging unit that receives reflection of the illumination light from the subject's eye and a light emitting unit for background illumination that is provided in the observation system and located below the subject's eye.

The ophthalmologic apparatus and camera device of the present disclosure can provide an ophthalmologic apparatus and a camera device which have a background illumination function and an imaging function for a subject's eye in a simple configuration.

DETAILED DESCRIPTION

First Embodiment

A first embodiment of the present disclosure will be described below with reference to the drawings. In the following description, a side of an ophthalmologic apparatus 10 facing a subject will be referred to as a front side, a side of the apparatus opposite to the front side (a side facing an examiner) as a rear side, a left side of the apparatus as viewed from the subject as a left side, and a side of the apparatus opposite to the left side as a right side. The description will be made on the assumption that the top and bottom of the ophthalmologic apparatus 10 are those of the ophthalmologic apparatus 10 shown in FIG. 1.

Figure 1:
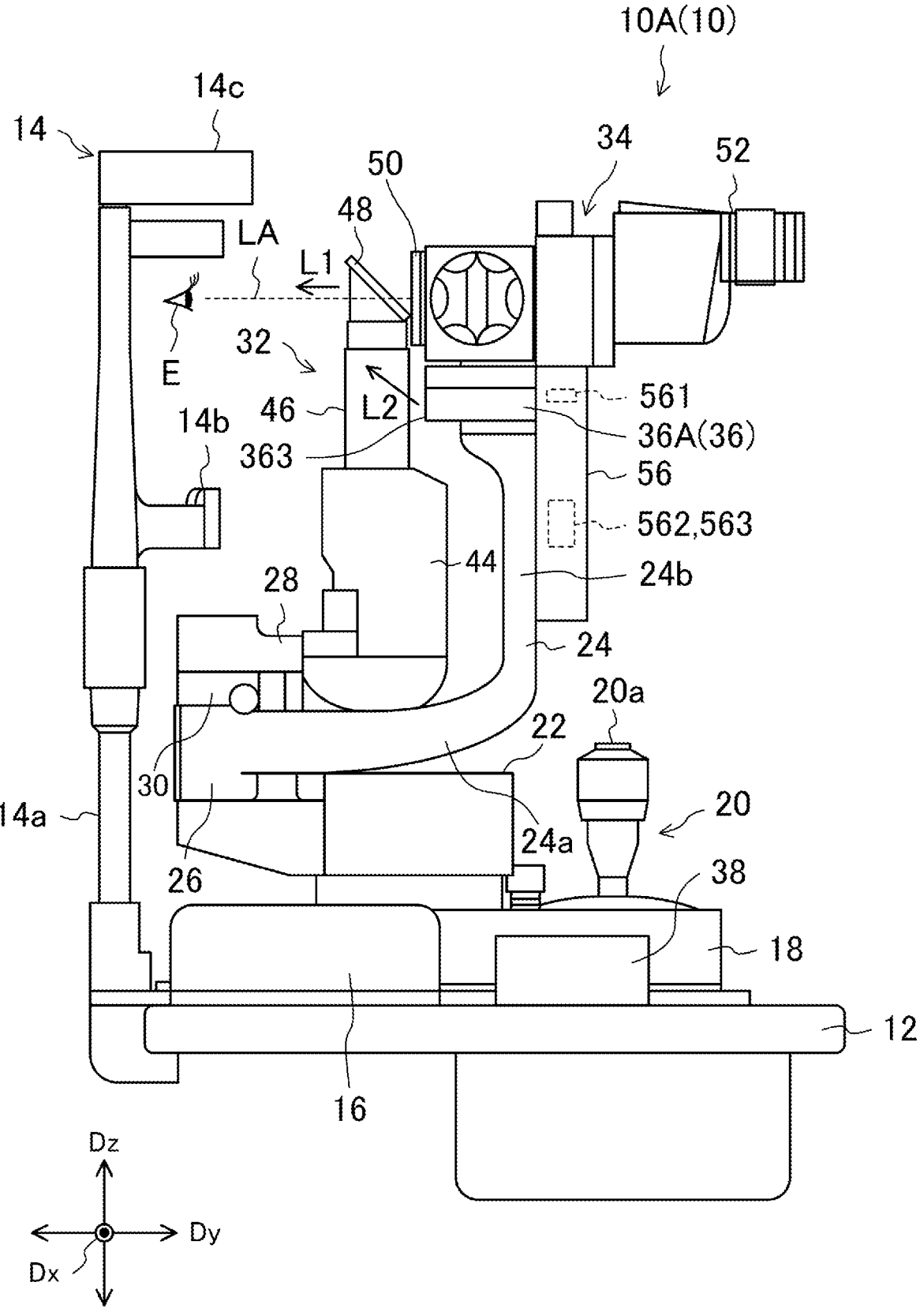
FIG. 1 is a side view of an ophthalmologic apparatus of a first embodiment of the present disclosure.

A configuration of the ophthalmologic apparatus 10 will be described first. FIG. 1 is a side view of the ophthalmologic apparatus 10A (10). As shown in FIG. 1, the ophthalmologic apparatus 10A of the present embodiment is a so-called slit lamp microscope of Zeiss type (Littman type). The ophthalmologic apparatus 10A includes a base 12, a face support part 14, an electric driver 16, a movable table 18, an operating lever 20, a first support member 22, a microscope support arm 24, a rotation shaft 26, a second support member 28, a rotation shaft 30, an illumination system 32, an observation system 34 (microscope unit), an illuminator 36 for background illumination, and a light source operation unit 38.

The base 12 is placed on an optometry table (not shown). The face support part 14 is provided above the base 12. The electric driver 16 and the light source operation unit 38 are provided on an upper surface of the base 12. Further, the base 12 holds the movable table 18 to be movable in horizontal directions (front-rear directions Dy and left-right directions Dx). The front-rear directions Dy include a forward direction toward the subject and a rearward direction away from the subject, and the left-right directions Dx are parallel to a pupillary distance of the subject.

The face support part 14 includes a pair of support posts 14a fixed to the base 12 and extending in the up-down direction, a chin rest 14b provided in the middle of the pair of support posts 14a in the up-down direction, and a forehead rest 14c provided at upper ends of the pair of support posts 14a in the up-down direction. The face support part 14 supports the face of the subject when the subject places their chin on the chin rest 14b and puts their forehead on the forehead rest 14c. Thus, the face support part 14 fixes the position of a subject's eye E. The face support part 14 fixes the subject's eye E at a position substantially above the rotation shafts 26 and 30.

The electric driver 16 is a moving mechanism that moves the movable table 18 on the base 12 in the horizontal directions (the left-right directions Dx and the front-rear directions Dy). The operating lever 20 is provided above a rear end part of the movable table 18 (closer to the examiner). The first support member 22 is provided on an upper surface of the movable table 18. The first support member 22 is movable in the up-down directions (movable up and down).

The electric driver 16 includes a plurality of motors (not shown) and a drive transmission mechanism (not shown) that converts rotation of each motor into driving force in the horizontal directions (Dx, Dy) and up-down directions Dz. The electric driver 16 has the function of moving the movable table 18 in the horizontal directions (Dx, Dy) and the function of moving the first support member 22 in the up-down directions Dz in response to the handling of the operating lever 20. Thus, the electric driver 16 can adjust the position of the first support member 22 (the illumination system 32 and the observation system 34) with respect to the subject's eye E.

The operating lever 20 is an operating member for manually moving the first support member 22 (the illumination system 32 and the observation system 34) in the horizontal directions (Dx, Dy) and the up-down directions Dz. For example, when the operating lever 20 is tilted in the front or rear direction Dy or the left or right direction Dx, the electric driver 16 moves the movable table 18 in the front or rear direction Dy or the left or right direction Dx. When the operating lever 20 is rotated about its axis, the electric driver 16 moves the first support member 22 in the up-down direction Dz. The operating lever 20 has a switch 20a for, for example, capturing images on the top of the operating lever 20.

The first support member 22 includes the microscope support arm 24. The microscope support arm 24 has a horizontal arm portion 24a and a vertical arm portion 24b and is formed in a substantially L-shape in side view as shown in FIG. 1.

A front end (closer to the subject's eye E) of the horizontal arm portion 24a is attached to be horizontally rotatable (rotatable on a horizontal plane as a rotation plane) on the first support member 22 via the rotation shaft 26 extending in the up-down direction Dz. The second support member 28 is attached to be horizontally rotatable via the rotation shaft 30 that is located on the extension of, i.e., substantially coaxial with, the rotation shaft 26 of the horizontal arm portion 24a.

The horizontal rotation of the microscope support arm 24 about the rotation shaft 26 and the horizontal rotation of the second support member 28 about the rotation shaft 30 may be manually achieved by the examiner or may be electrically achieved by the examiner using an electric rotation mechanism (not shown).

The observation system 34, which is a microscope unit, is attached to an upper end of the vertical arm portion 24b. The illumination system 32 is provided on the second support member 28.

The illumination system 32 includes a slit lamp 44 that emits first illumination light L1 and a deflection optical system 46. The slit lamp 44 emits slit light as the first illumination light L1 toward the deflection optical system 46. The deflection optical system 46 is provided above the slit lamp 44 and has, above the slit lamp 44, a deflection unit 48 that deflects the first illumination light L1 to the subject's eye E. The deflection unit 48 is comprised of a deflection optical element such as a mirror (reflecting mirror) or a prism. The deflection unit 48 deflects (guides) the first illumination light L1 emitted from the slit lamp 44 toward the subject's eye E. Thus, the first illumination light L1 is applied to the subject's eye E. In this embodiment, a prism is used as the deflection optical element. The slit lamp 44 and the deflection optical system 46 are not limited to those shown in FIG. 1 and are not limited to have particular shape, structure, and arrangement as long as they are applicable in the slit lamp microscope of Zeiss type.

The illumination system 32 has the function of horizontally rotating about the rotation shaft 30 integrally with the second support member 28. The face support part 14 fixes the subject's face so that the subject's eye E is positioned substantially above the rotation shaft 30. Thus, the electric driver 16 supports the illumination system 32 so as to be rotatable about the subject's eye E with an irradiation direction of the first illumination light L1 kept toward the subject's eye E. This configuration allows the illumination system 32 to adjust the irradiation direction (incident angle) of the first illumination light L1 with respect to the subject's eye E.

The observation system 34 is arranged opposite to the subject's eye E across the illumination system 32. The observation system 34 is used to observe the subject's eye E irradiated with the first illumination light L1 emitted from the illumination system 32 and various kinds of light emitted from the illuminator 36 described later. The observation system 34 includes an objective lens 50, which is a light receiving section, arranged at a front end (an end closer to the subject's eye E) of the observation system 34. The observation system 34 further includes an eyepiece 52 arranged at a rear end (an end closer to the examiner) of the observation system 34. Reference character LA in FIG. 1 is an axis connecting the subject's eye E and the objective lens 50 (light receiving section) and is an optical axis (observation axis) of the objective lens 50.

For example, the observation system 34 adjusts magnification or perform any other adjustments so that the light received by the objective lens 50 is guided toward the examiner (to the rear side of the ophthalmologic apparatus 10A) to be emitted from the eyepiece 52. The observation system 34 has the function of horizontally rotating about the rotation shaft 26 integrally with the microscope support arm 24. Thus, the observation system 34 can adjust the direction of observation of the subject's eye E.

The observation system 34 of the present embodiment includes a camera device 56 that captures images of the subject's eye E via the optical system of the observation system 34. The observation system 34 includes the camera device 56 arranged opposite to the subject's eye E (or the objective lens 50). The camera device 56 is, for example, a digital camera. The camera device 56 has an elongated shape. The camera device 56 is detachably attached to a casing of the observation system 34 (the vertical arm portion 24b in the example of FIG. 1) so that its long axis is parallel to the up-down direction Dz.

The camera device 56 includes an imaging unit 561 (not shown) that receives the first illumination light L1 reflected from the subject's eye E and captures images, a power supply circuit 562, and a control circuit 563. The imaging unit 561 is an imaging element such as a complementary metal-oxide semiconductor (CMOS) image sensor or a charge-coupled device (CCD) image sensor. Part of the first illumination light L1 incident on the camera device 56 via the objective lens 50 is guided to the imaging unit 561 by a half mirror and imaged. Another part of the first illumination light L1 is guided toward the eyepiece 52. The power supply circuit 562 supplies driving power to the camera device 56. The power supply circuit 562 may be configured as a circuit that distributes part of the power supplied from the ophthalmologic apparatus 10A to respective functional units or may be configured to include a battery, a transformer, or a power generation circuit.

Figure 3:
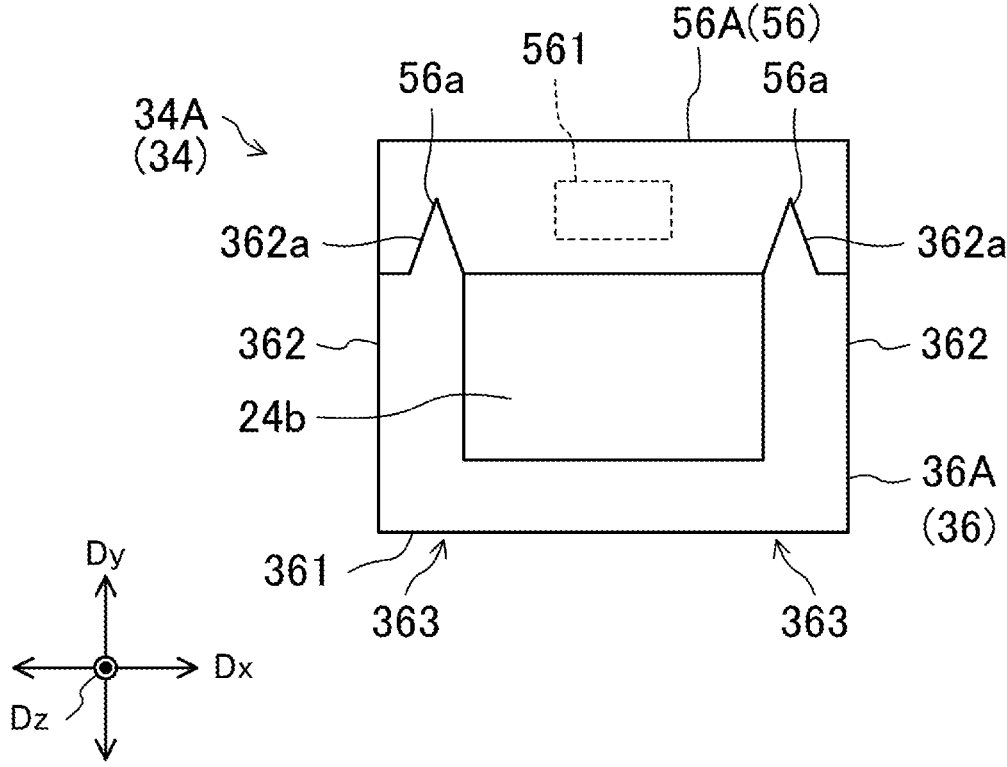
FIG. 3 is a schematic plan view illustrating a wide camera device and a thin camera device (first variation of the first embodiment) to each of which an illuminator is attached.
Figure 3:
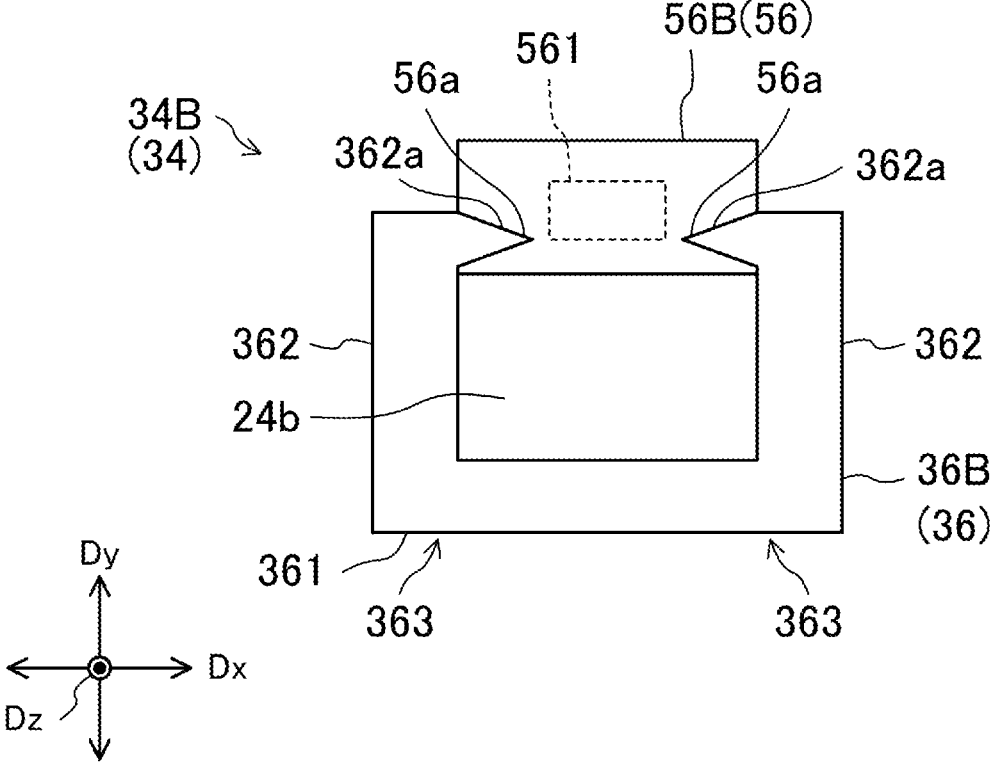

In the ophthalmologic apparatus 10A, the illuminator 36 is provided in the observation system 34 and located below the subject's eye E. FIG. 3 is a schematic plan view illustrating an observation system 34A (34) having an illuminator 36A attached to the wide camera device 56 of the present embodiment. The ophthalmologic apparatus 10A of FIG. 1 has the observation system 34A. The illuminator 36A of the observation system 34A includes an elongated illuminator body 361 having a plurality of light emitting units 363 (which will be described in detail later) for background illumination, and arms 362 extending rearward from both ends of the illuminator body 361. The illuminator body 361 is connected to each of the arms 362 at a substantially right angle, and thus the illuminator 36A is substantially U-shaped in plan view.

The camera device 56 of the observation system 34A of the present embodiment includes the imaging unit 561 and the light emitting units 363 described above. The illuminator 36A is connected and fixed to the camera device 56. For example, the illuminator 36A is connected to the camera device 56 by sandwiching the vertical arm portion 24b of the observation system 34A between the arms 362 of the U-shaped illuminator body 361, and is configured to be removably inserted in (detachably attached to) the camera device 56 from the side of the subject's eye E, the camera device 56 being wider than the vertical arm portion 24b in a movable direction of the illumination system 32 when viewed from the subject's eye E. In the observation system 34A, the illuminator 36A is fixed to the camera device 56 when insertion portions 362a (e.g., jacks) provided at the ends of the arms 362 are connected to receiver portions 56a (e.g., receptacles) provided in the camera device 56. The illuminator 36A may be configured such that a lower surface of the illuminator body 361 is supported by a support protrusion protruding forward from a front surface of the vertical arm portion 24b.

The illuminator 36A can receive power supplied from the power supply circuit 562 of the camera device 56 via a distribution cable passing through the inside of the arms 362. A control circuit of the illuminator 36 may share a circuit board with the control circuit 563 of the camera device 56 or may be provided on a circuit board different from the circuit board of the control circuit 563 of the camera device 56 and placed in the casing of the camera device 56. When the circuit board of the control circuit of the illuminator 36 is placed in the casing of the camera device 56, the illuminator 36 and the camera device 56 can be reduced in size as a whole.

Figure 2:
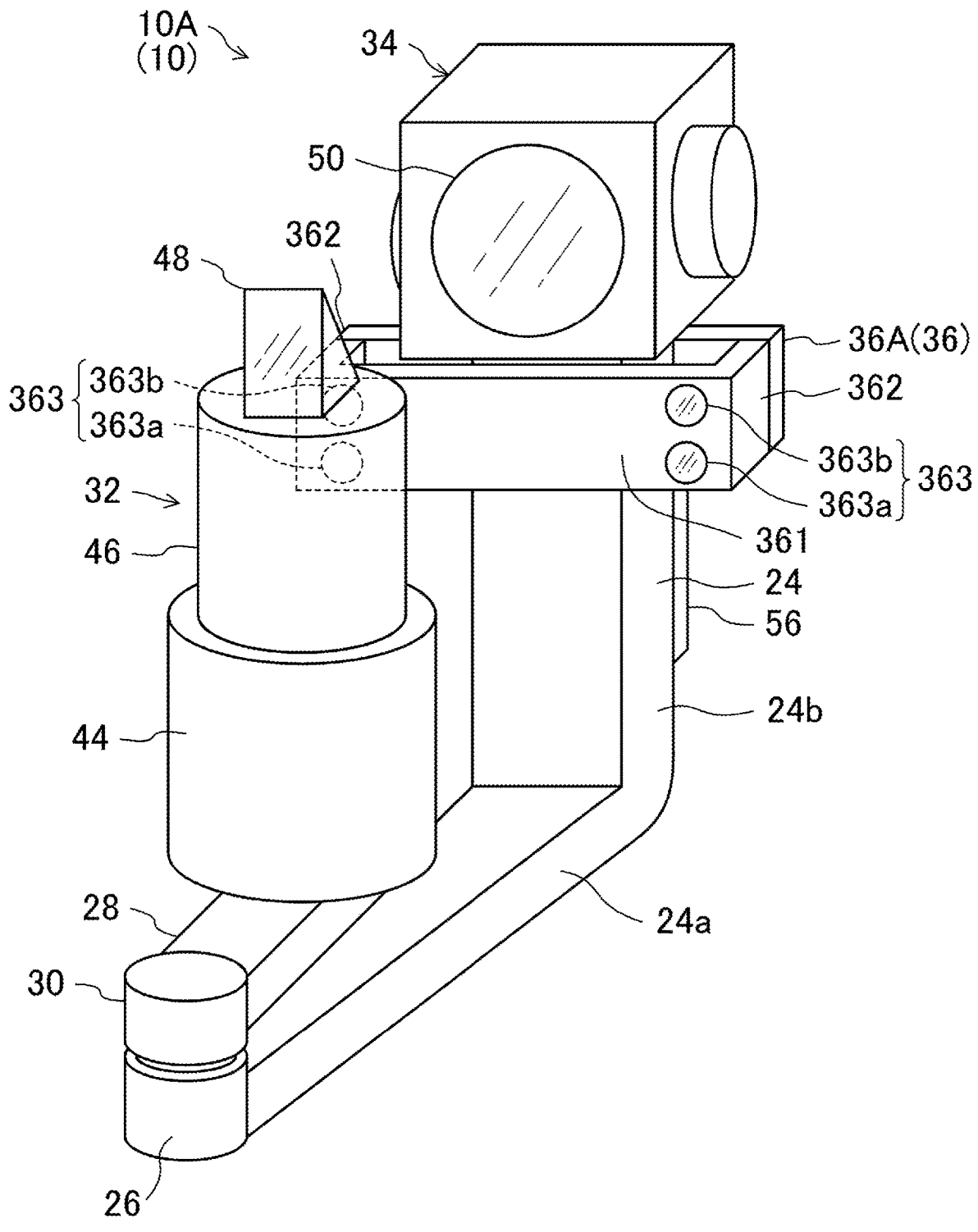
FIG. 2 is a perspective view of an illumination system and observation system of the ophthalmologic apparatus of the first embodiment as viewed from a subject.

The light emitting units 363 include light sources capable of selectively emitting different types of light (e.g., three types of light including visible light, infrared light, and excitation light) to the subject's eye E. As shown in FIG. 2, each of the light emitting units 363 of the present embodiment includes an infrared light source 363a capable of emitting infrared light and a visible light source 363b capable of emitting visible light. The infrared light source 363a and visible light source 363b of the light emitting unit 363 are vertically arranged on the front side of the illuminator body 361.

The light source operation unit 38 is provided on a rear part (a part closer to the examiner) of the upper surface of the base 12. As will be described in detail later, the light source operation unit 38 is used by the examiner to turn the slit lamp 44 on or off, adjust the light amount of the slit lamp 44, turn the light emitting units 363 on or off, and adjust the light amount of the light emitting units 363.

Figure 4:
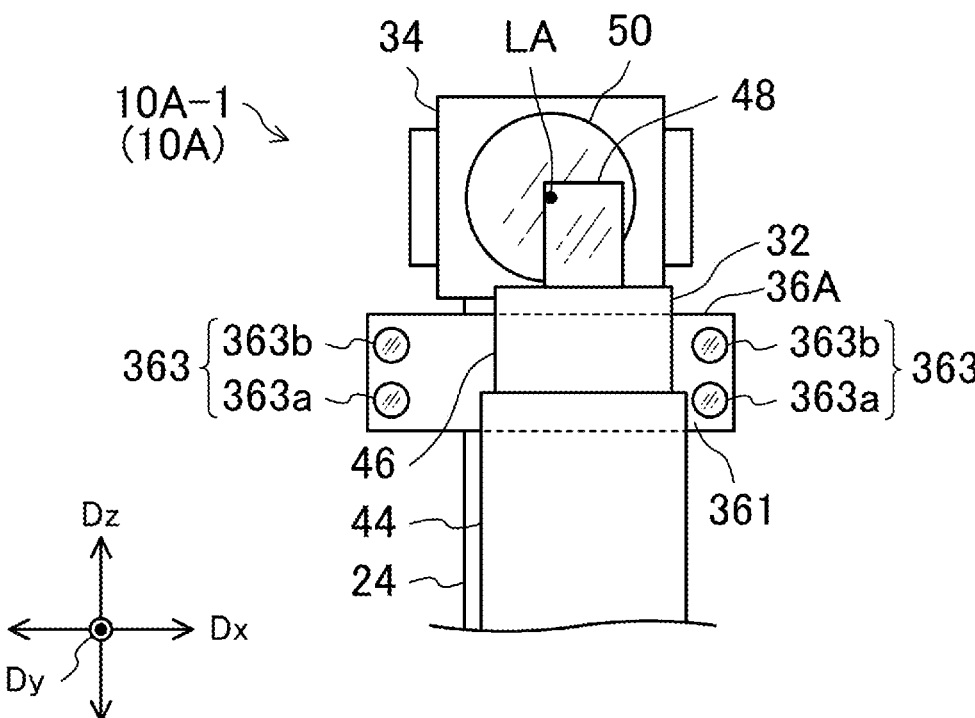
FIG. 4 is a front view illustrating the illumination system of the ophthalmologic apparatus of the first embodiment located at different positions.
Figure 4:
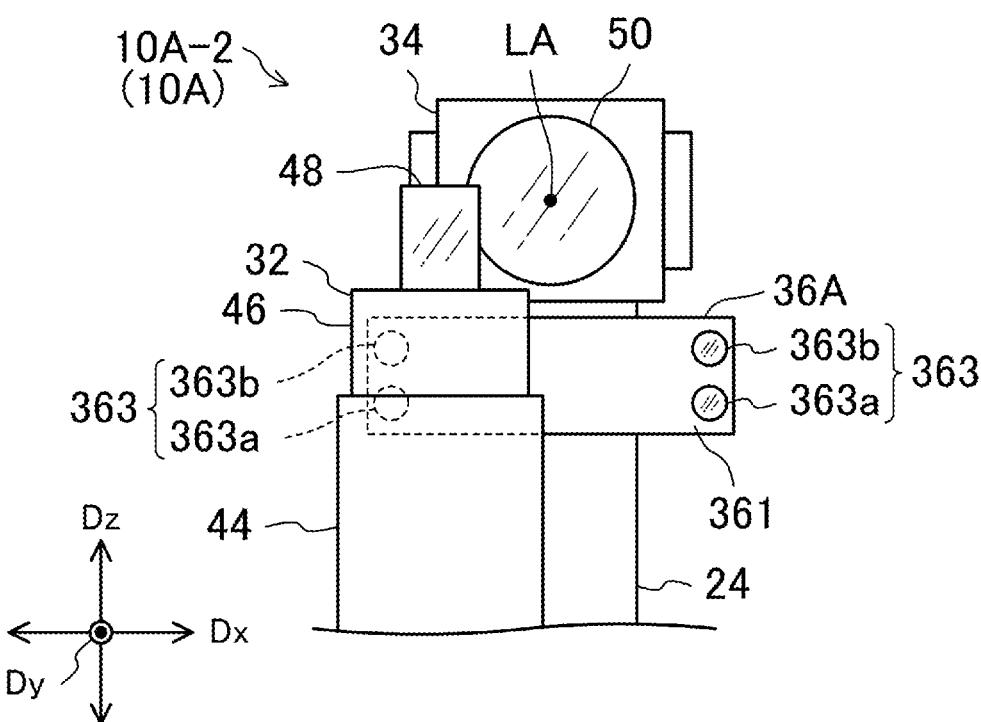

FIG. 4 is a front view of the illumination system 32 and the observation system 34 as viewed from the subject (subject's eye E). FIG. 4 illustrates an ophthalmologic apparatus 10A-1 and an ophthalmologic apparatus 10A-2 which are different in relative position of the illumination system 32 with respect to the observation system 34. The light emitting units 363 are arranged in the left-right direction Dx which is a movable direction of the illumination system 32 when viewed from the subject's eye E. In other words, the illumination system 32 is movable in the arrangement direction of the light emitting units 363. The light emitting units 363 of the present embodiment have the same type of light source, i.e., the infrared light sources 363a and the visible light sources 363b, at both end portions on the right side and the left side in a front view. Each light emitting unit 363 includes a single infrared light source 363a and a single visible light source 363b. The visible light source 363b is arranged above the infrared light source 363a in each light emitting unit 363.

Figure 5:
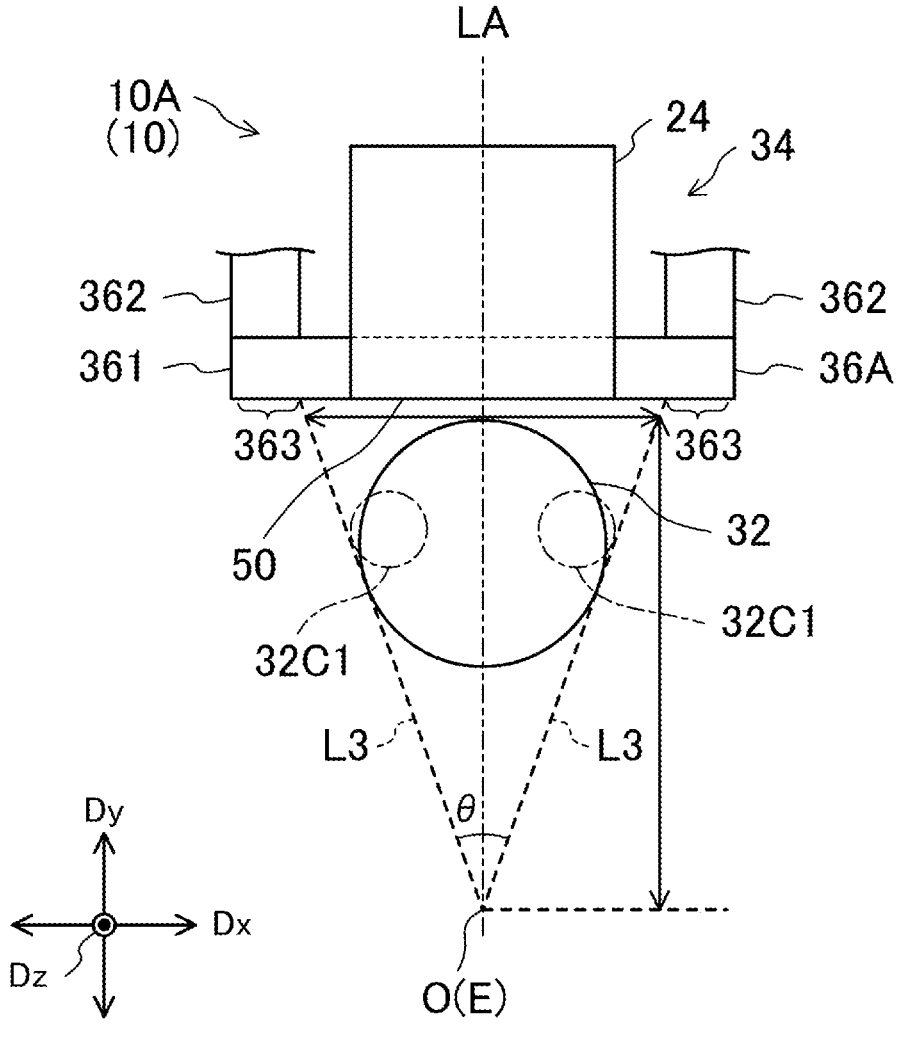
FIG. 5 is a plan view illustrating a positional relationship between the subject's eye and the illumination system and light emitting units of the ophthalmologic apparatus of the first embodiment.

FIG. 5 is a plan view illustrating the illumination system 32 and the observation system 34. In the ophthalmologic apparatus 10A of FIG. 5 viewed in plan in the direction of the rotation shaft 30 of the illumination system 32, the light emitting units 363 are arranged on the outside of an angular range of a light-blocking angle θ that is formed between two tangents L3 to the illumination system 32 located on the observation axis LA connecting the objective lens 50 serving as the light receiving section of the observation system 34 and the origin O which is the position of the subject's eye E (a reference position of the subject's eye E, such as the approximate center of the subject's eye E or the position of the anterior segment). Thus, as shown in FIG. 5, when the illumination system 32 is located substantially on the observation axis LA, the subject's eye E can be irradiated with second illumination light L2 as background illumination light from both of the light emitting units 363 arranged at both end portions of the illuminator 36 in the left-right direction Dx.

Figure 6:
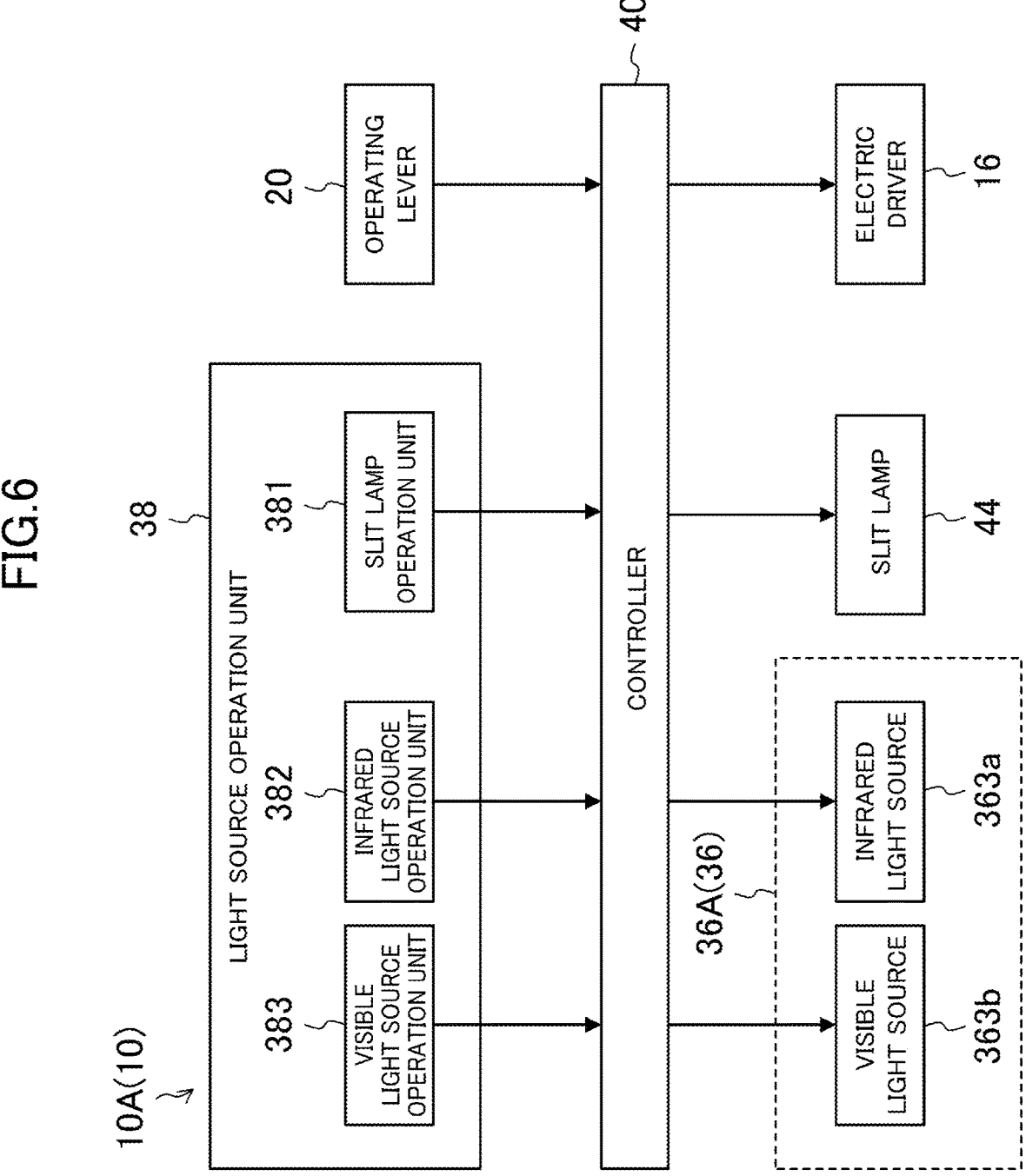
FIG. 6 is a control block diagram of the ophthalmologic apparatus.

FIG. 6 is a schematic diagram of the light source operation unit 38 and a controller 40 included in the ophthalmologic apparatus 10A (10). The light source operation unit 38 includes a slit lamp operation unit 381, an infrared light source operation unit 382, and a visible light source operation unit 383. The ophthalmologic apparatus 10A further includes a storage (which is not shown and may be referred to as a storage medium) that stores a control program for executing the functions of the ophthalmologic apparatus 10A.

The slit lamp operation unit 381 receives an input for turning on or off the slit lamp 44 and an input for adjusting the amount of the first illumination light (slit light) emitted from the slit lamp 44. The infrared light source operation unit 382 receives an input for turning on or off the infrared light source 363a and an input for adjusting the amount of the infrared light emitted from the infrared light source 363a. The visible light source operation unit 383 receives an input for turning on or off the visible light source 363b and an input for adjusting the amount of the visible light emitted from the visible light source 363b.

The controller 40 is provided, for example, inside the movable table 18 (or outside the ophthalmologic apparatus 10A) and controls the operation of the components of the ophthalmologic apparatus 10A in a centralized manner. The controller 40 is, for example, an arithmetic device such as a personal computer, and includes an arithmetic circuit including various processors and memories. The various processors include a central processing unit (CPU), a graphics processing unit (GPU), an application specific integrated circuit (ASIC), and a programmable logic device, for example, a simple programmable logic device (SPLD), a complex programmable logic device (CPLD), and a field programmable gate array (FPGA). Various functions of the controller 40 may be achieved by one processor or a plurality of processors of the same type or different types.

The controller 40 can drive the electric driver 16 to move the movable table 18 in the front or rear direction Dy or the left or right direction Dx when the operating lever 20 is tilted in the front or rear direction Dy or the left or right direction Dx, and can drive the electric driver 16 to move the first support member 22 in the up or down direction Dz when the operating lever 20 is rotated about the axis.

The controller 40 further controls the turning on/off of the light sources including the slit lamp 44, the infrared light sources 363a, and the visible light sources 363b and the adjustment of the amount of light emitted from each of the light sources in accordance with the inputs of an on/off operation and a light amount adjustment operation to the light source operation unit 38. Thus, the examiner can easily switch between on and off of the light sources corresponding to the on/off operation and can adjust the amount of the light emitted from the light sources corresponding to the light amount adjustment operation. The controller 40 functions as a light source controller of the present invention. This configuration allows the switching between the light sources, the adjustment of the light amount, or other control more easily than when the switching and the adjustment are manually performed (e.g., by changing a filter or other techniques).

Referring back to FIG. 4 illustrating the ophthalmologic apparatus 10A-1 (10A), the illuminator 36A which is wide in the left-right direction Dx is attached to the observation system 34, and the illumination system 32 is located substantially on the observation axis LA. In the ophthalmologic apparatus 10A-1, even if the observation system 34 is displaced to some extent in the left-right direction Dx from the observation axis LA, the subject's eye E can be irradiated with the second illumination light L2 from the light emitting units 363 at the left and right end portions.

When the illumination system 32 has moved relative to the observation system 34 as in the ophthalmologic apparatus 10A-2 (10A) shown in FIG. 4, the illumination system 32 may block the light emitted from one of the left and right light emitting units 363. However, the ophthalmologic apparatus 10A-2 (10A) of the present embodiment includes a plurality of light emitting units 363 arranged in the left-right direction Dx. Thus, the ophthalmologic apparatus 10A-2 can irradiate the subject's eye E with the second illumination light L2 emitted from at least one of the light emitting units 363 (the light emitting unit 363 on the right in FIG. 4) regardless of the position of the illumination system 32.

Figure 7:
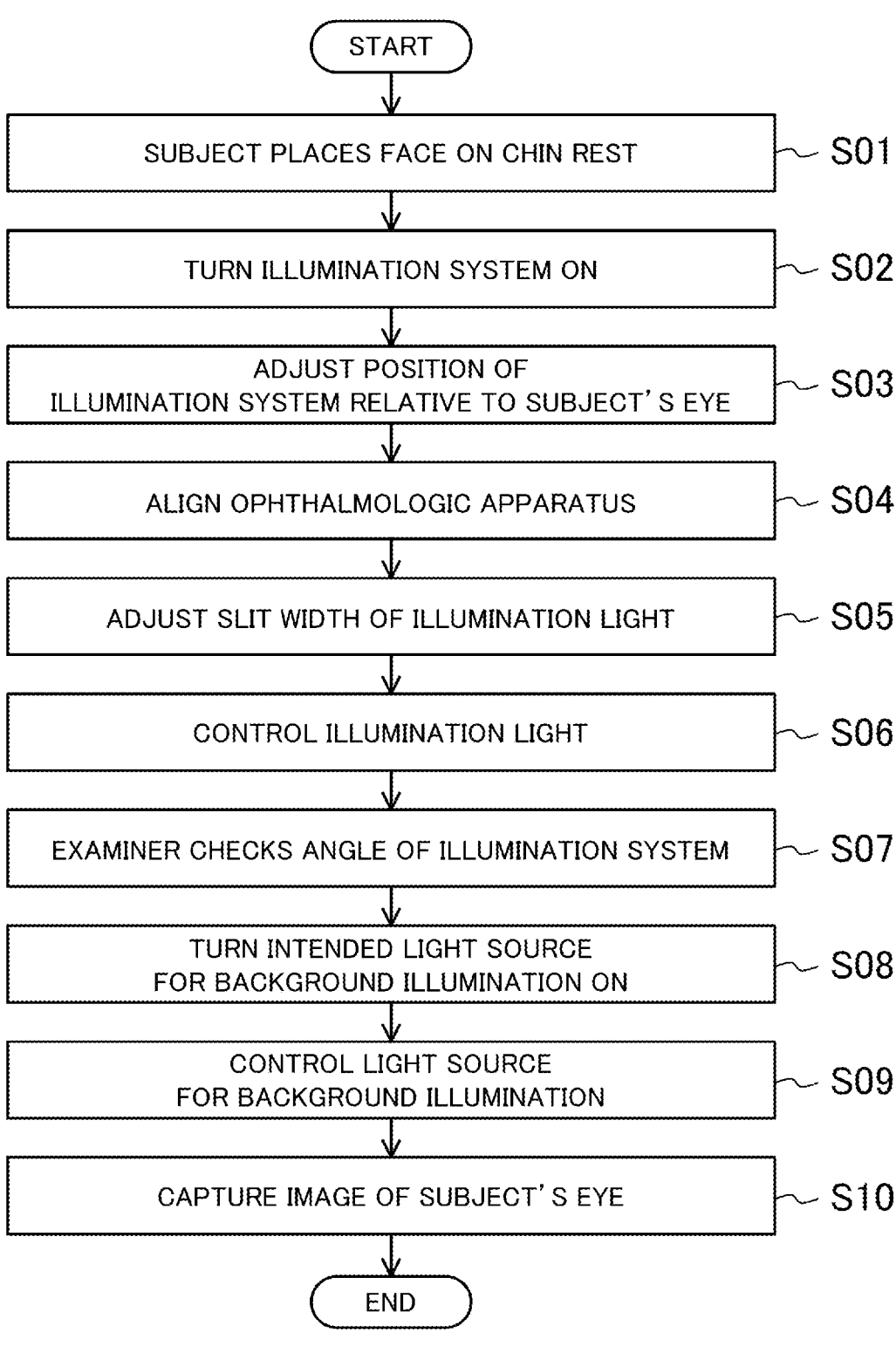
FIG. 7 is an operation flowchart of the ophthalmologic apparatus of the first embodiment.

An example of an operation flowchart of the ophthalmologic apparatus 10A will be described below with reference to FIG. 7. The flowchart of FIG. 7 shows an example in which the ophthalmologic apparatus 10A is semi-manually operated using the operating lever 20, the light source operation unit 38, or the like (or semi-automatically operated by the controller 40) in Steps S08 and S09, but the other processes may be performed manually or automatically by the controller 40.

First, in Step S01, the subject places their chin on the chin rest 14b so that their face is supported and that the position of the subject's eye E is fixed. In Step S02, a user such as the examiner turns on the power supply of the illumination system 32 (switches the power supply to "ON") by, for example, handling the operating lever 20.

In Step S03, the user adjusts the position and angle of the illumination system 32 relative to the position of the subject's eye E by, for example, handling the operating lever 20. In Step S04, the user adjusts alignment of the ophthalmologic apparatus 10A. The user adjusts a slit width of the first illumination light L1 to be applied to the subject's eye E in Step S05 and performs light control such as adjustment of brightness of the first illumination light L1 in Step S06, via the light source operation unit 38, for example.

In Step S07, the user checks the angle of the first illumination light L1 emitted from the illumination system 32 to the subject's eye E with respect to the observation axis LA, and the ophthalmologic apparatus 10A adjusts the position of the illumination system 32 so that the illumination system 32 is located at any position (i.e., at any angle with respect to the observation axis LA) in accordance with the user's input.

In Step S08, the controller 40 turns on (or switches to "ON") any of the light sources for background illumination according to the input from the user to the light source operation unit 38. Which of the infrared light source 363*a* or the visible light source 363*b* of the light emitting unit 363 is to be turned on may be manually set by the user or may be automatically set by the controller 40.

In Step S09, the controller 40 controls the light emitted from the light source for background illumination that is turned on. The ophthalmologic apparatus 10A of the present embodiment has the function of controlling the light from the light emitting unit 363 depending on the relative position between the illumination system 32 and the light emitting unit 363. The user controls the light via the light source operation unit 38 while checking an image of the subject's eye E using, for example, the eyepiece 52 (see FIG. 1) or an external monitor (not shown).

The controller 40 can turn on the left and right light emitting units 363 in accordance with the input from the user to the light source operation unit 38 when the illumination system 32 is on the observation axis LA and the subject's eye E can be irradiated with the second illumination light L2 emitted from the left and right light emitting units 363 (see the ophthalmologic apparatus 10A-1 in FIG. 4).

For the observation of the subject's eye E, the illumination system 32 mainly applies the first illumination light L1 to the subject's eye E from a position deviated (separated) from the observation axis LA connecting the subject's eye E and the objective lens 50, which is the light receiving section of the observation system 34, and in a direction inclined with respect to the observation axis LA. Thus, when the illumination system 32 is deviated leftward (or rightward) from the observation axis LA and the second illumination light L2 emitted from one of the light-emitting units 363 is blocked (see the ophthalmologic apparatus 10A-2 in FIG. 4), the one of the light emitting units 363 whose second illumination light L2 is blocked is turned off. This can keep the ophthalmologic apparatus 10A from wasting power.

In Step S10, the camera device 56 is operated by the input to the operating lever 20, and an image of the subject's eye E is captured. The camera device 56 stores the captured image in the storage or the like of the ophthalmologic apparatus 10A.

The ophthalmologic apparatus 10A of the present embodiment has been described above. The known ophthalmologic apparatus disclosed by Japanese Unexamined Patent Publication No. 2020-141998 is not easy to handle because an operator, such as an ophthalmologist or a nurse, needs to operate an illuminator adjuster located away from their hands to turn on or off the power supply for background illumination, control the light, or conduct other control. In some cases, the power supply of the illuminator for background illumination is configured to receive power through a wire different from a wire used between the power supply and other components of the ophthalmologic apparatus. Specifically, wires of two systems are drawn out from the ophthalmologic apparatus, causing an increase in space for installing the ophthalmologic apparatus, an increase in wiring costs, or being uneconomical or other problems.

The ophthalmologic apparatus 10A of the present embodiment includes the illuminator 36A and the camera device 56 connected to each other. This configuration allows the user to adjust the background illuminator at hand, and the power supply for the illuminator emitting the second illumination light L2 can also be used as the power supply for the camera device 56, saving the number of wires and space. In the known configuration, the illuminator for background illumination is attached to the top of the observation system, and an upper part of the casing of the observation system is positioned at a relatively high level. This makes it difficult to mount a device such as an applanation tonometer in some cases. However, according to the ophthalmologic apparatus 10A, it is possible to share at least one of the circuit board of the control circuit and the circuit board of the power supply circuit between the illuminator 36 and the camera device 56, and is thus possible to achieve one or more of the following advantages, that is, cost reduction, reduction of the number of wires, and downsizing (space saving) while having the illumination function and the imaging function.

It has been described in the present embodiment that the illuminator 36A is removably inserted (detachably attached) from the side of the subject's eye E, but the present invention is not limited to this example. For example, the illuminator 36A may be removably inserted in (detachably attached to) the camera device 56 from the side of the examiner, right or left, or from the above of the ophthalmologic apparatus 10, or any other direction.

First Variation of First Embodiment

As described for the observation system 34A of FIG. 3, it has been described in the present embodiment that the illuminator 36 is removably inserted in the camera device 56 which is wider than the vertical arm portion 24*b* from the side of the subject's eye E. As shown in FIG. 3, the observation system 34B of the ophthalmologic apparatus 10A may have the camera device 56 which is thinner in the left-right direction than the illuminator 36B, and the insertion portions 362*a* may be connected to the receiver portions 56*a* formed on the left and right side surfaces of the camera device 56. This configuration can prevent unintentional drop of the illuminator 36B when the illuminator 36B is connected to the camera device 56.

Second Variation of First Embodiment

Figure 8:
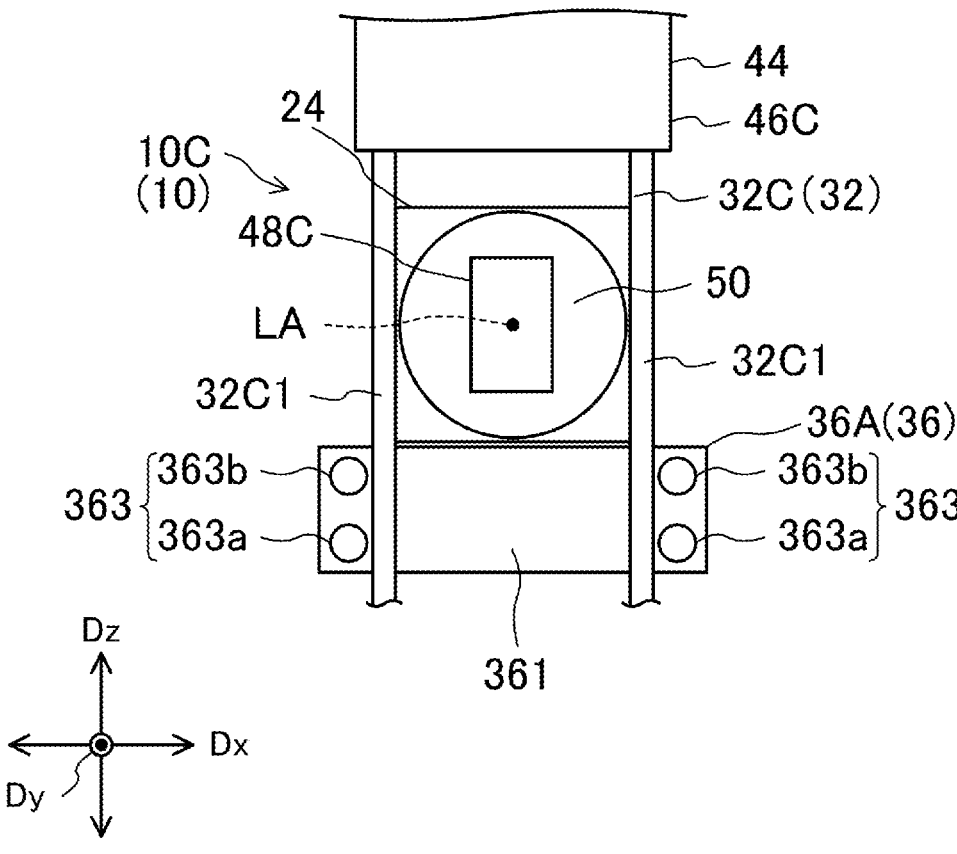
FIG. 8 is a diagram illustrating a second variation of the ophthalmologic apparatus of the first embodiment.

FIG. 8 is a front view of an ophthalmologic apparatus 10C (10) having an illumination system 32C (32) that is taller than the observation system 34 shown in FIG. 1. In the description of the ophthalmologic apparatus 10C, the same components as those of the ophthalmologic apparatus 10A are denoted by the same reference characters and will not be described or will be described simply. The ophthalmologic apparatus 10C includes a so-called tower type illumination system 32C instead of the illumination system 32A of the first embodiment. The illumination system 32C includes two support posts 32C1 spaced apart from each other to leave space around the observation axis LA in front view as shown in FIG. 8. Although not shown in detail, a lower portion of each support post 32C1 is supported by and connected to the second support member 28 shown in FIG. 1 to be rotatable about the rotation shaft 30. In the ophthalmologic apparatus 10C, the slit lamp 44 and an illumination optical system 46C are arranged above the support posts 32C1. The ophthalmologic apparatus 10C has the illumination optical system 46C of the illumination system 32C located below the slit lamp 44 and also has a deflection unit 48C that deflects the first illumination light L1 toward the subject's eye E below the slit lamp 44. The deflection unit 48C is supported by the second support member 28 of the illumination system 32C (see also FIG. 1), but details of the support structure are not shown. The deflection unit 48C having the same function as the deflection unit 48 described above is, for example, a mirror (reflecting mirror) or a prism. The deflection unit 48C deflects (guides) the first illumination light L1 emitted from the slit lamp 44 toward the subject's eye E.

FIG. 5 illustrates a positional relationship among the support posts 32C1 (illustrated by a dot-dash line) of the ophthalmologic apparatus 10C, the subject's eye E, and the light emitting units 363. In the ophthalmologic apparatus 10C viewed in plan in the direction of the rotation shaft 30 of the illumination system 32 (32C), the light emitting units 363 are arranged on the outside of an angular range of a light-blocking angle θ that is formed between two tangents L3 to the illumination system 32 (32C) located on the observation axis LA connecting the objective lens 50 serving as the light receiving section of the observation system 34 and the origin O which is the position of the subject's eye E. Thus, when the tower type illumination system 32C is located on the observation axis LA, the subject's eye E can be irradiated with the second illumination light L2 as the background illumination light from both of the light emitting units 363 arranged at both end portions of the illuminator 36A in the left-right direction Dx.

When the tower type illumination system (e.g., the illumination system 32C) is applied to an ophthalmologic apparatus having the light emitting unit for background illumination arranged above the observation system, the illumination light emitted from the light emitting unit may be blocked by the illumination system depending on a rotation position of the illumination system and may fail to illuminate the subject's eye E sufficiently. However, although the tower type illumination system 32C is applied, the ophthalmologic apparatus 10C including the illuminator 36A of the present embodiment can avoid the light of the illuminator for background illumination from being blocked by the illumination system, can keep the subject's eye E from being shaded by the eyelid, and can irradiate the subject's eye E with the second illumination light L2 as the background illumination light from any of the light emitting units 363, allowing more accurate observation of the subject's eye E.

Second Embodiment

Figure 9:
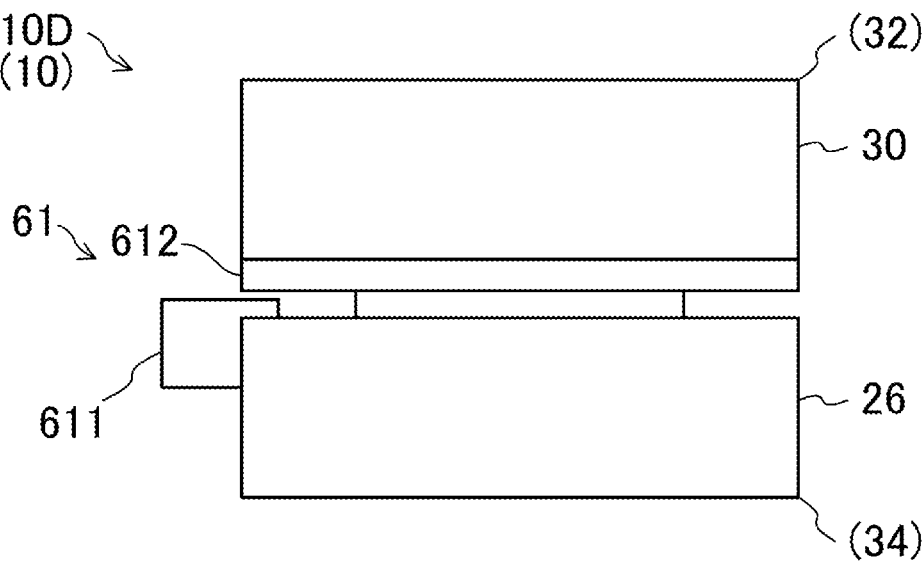
FIG. 9 is an enlarged view of a rotation shaft of an ophthalmologic apparatus of a second embodiment with an optical encoder attached thereto and a rotation shaft of a first variation of the second embodiment with a magnetic encoder attached thereto.
Figure 9:
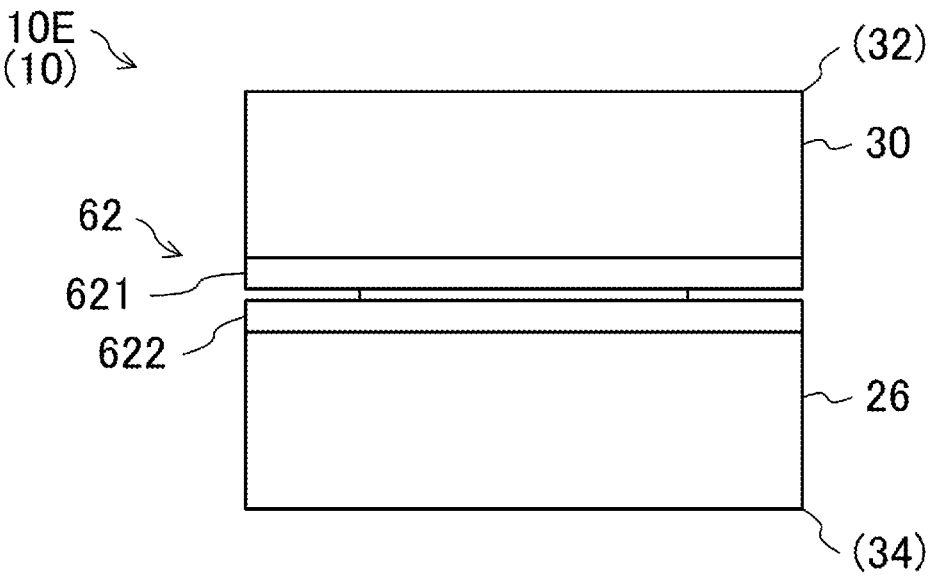

A second embodiment of the present disclosure will be described below. An ophthalmologic apparatus 10D of the second embodiment automatically controls second illumination light emitted from a light source for background illumination. FIG. 9 shows rotation shafts 26 and 30 of an ophthalmologic apparatus 10D and rotation shafts 26 and 30 of an ophthalmologic apparatus 10E in an enlarged scale. An optical encoder 61 (position detection unit) is attached to the rotation shafts 26 and 30 of the ophthalmologic apparatus 10D, and a magnetic encoder 62 (position detection unit) is attached to the rotation shafts 26 and 30 of the ophthalmologic apparatus 10E. In the second embodiment, the ophthalmologic apparatus 10D will be described. In the description of the ophthalmologic apparatus 10D, the same components as those of the ophthalmologic apparatus 10A are denoted by the same reference characters and will not be described or will be described simply.

Most part of the configurations of the ophthalmologic apparatus 10D are the same as those of the ophthalmologic apparatus 10A shown in FIG. 1. The ophthalmologic apparatus 10D includes the optical encoder 61 attached to the rotation shafts 26 and 30. The optical encoder 61 may be a rotary encoder, for example, and includes an optical sensor 611 and a slit disk 612. The slit disk 612 is disposed coaxially with the rotation shafts 26 and 30, has a flat plate shape, and is provided with two or more slits (openings or cutouts) arranged at intervals in the circumferential direction in an outer peripheral edge portion. The optical sensor 611 is a light projecting/receiving sensor having a light projecting section and a light receiving section as an integrated unit or separate units. The optical sensor 611 irradiates the slit disk 612 with light at portions where the slits are arranged in the radial direction and receives light reflected or transmitted by the slit disk 612. A controller 40 (see FIG. 6) of the ophthalmologic apparatus 10D can receive a light detection signal from the optical sensor 611 and can detect the rotation angles of the rotation shafts 26 and 30. Thus, the controller 40 can detect the rotation angle of the illumination system 32 with respect to the observation system 34 using the optical encoder 61.

Figure 10:
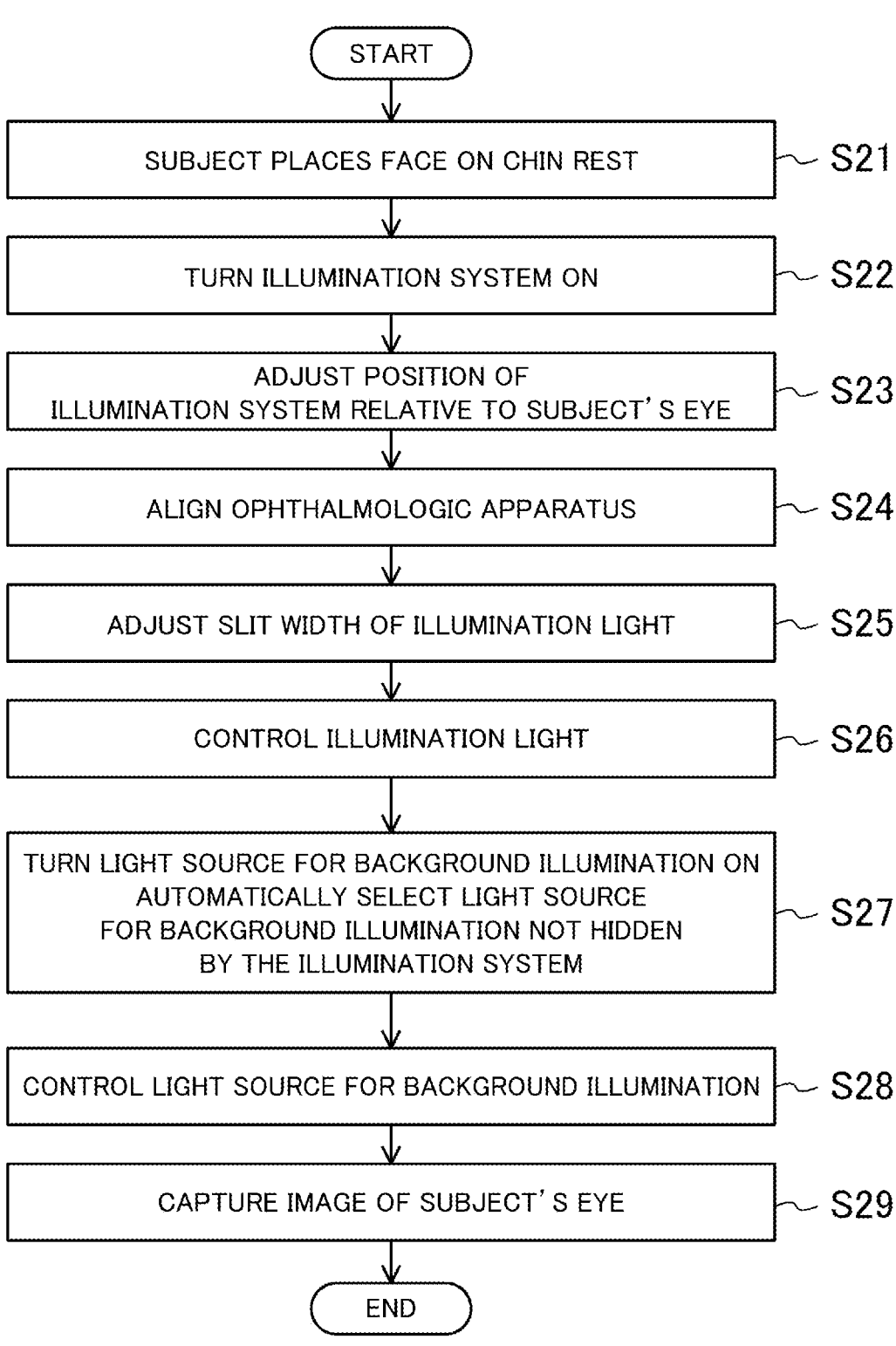
FIG. 10 is an operation flowchart of the ophthalmologic apparatus of the second embodiment.

An example of an operation flowchart of the ophthalmologic apparatus 10 will be described with reference to FIG. 10. In the flowchart of FIG. 10, the processes or operations of Steps S21, S22, S23, S24, S25, and S26 are the same as those of Steps S01, S02, S03, S04, S05, and S06. The process of Step S29 is the same as the process of Step S10.

In Step S27, the ophthalmologic apparatus 10D turns on (or switches to "ON") a power supply of a light source for background illumination according to the input from the user to the light source operation unit 38. The ophthalmologic apparatus 10D has the light control function of controlling the light emitted from the light emitting units 363 depending on the relative position between the illumination system 32 and the light emitting units 363. The light control includes on/off switching of the light emitting units 363 for the emission of the second illumination light L2 and the control of the amount of the light. As an example of the light control, the controller 40 detects, by the optical encoder 61, the relative position (rotation angle) of the illumination system 32 with respect to the observation system 34 adjusted in Step S23. Regarding the light emitting units 363 that are light sources for background illumination of the ophthalmologic apparatus 10A shown in FIG. 4, for example, the controller 40 has the function of automatically selecting and turning on one of the light emitting units 363 whose light is not blocked by the illumination system 32 (not shaded by the illumination system 32) and turning off the other light emitting unit 363 whose light is blocked by the illumination system 32. The light emitting unit 363 that is turned on emits the second illumination light L2 (see FIG. 1).

The ophthalmologic apparatus 10D has correspondence information in which the rotation angles of the illumination system 32 and the observation system 34 are associated with light block information indicating how much the second illumination light L2 emitted from each light emitting unit 363 reaches the subject's eye E. The correspondence information is stored in advance in the storage. Alternatively, the storage stores predetermined angles of the rotation angles as threshold information for turning on or off the light emitting units 363. For example, as shown in the ophthalmologic apparatus 10A-1 of FIG. 4, when the illumination system 32 hides none of the light emitting units 363 as viewed from the subject's eye E or partially hides the light emitting units 363 (e.g., 80% or half of the light emitting unit 363 remains unhidden) as viewed from the subject's eye E, the controller 40 can perform control to turn the light emitting units 363 on.

The ophthalmologic apparatus 10D may be configured such that which of the infrared light source 363a or the visible light source 363b of the light emitting unit 363 is to be turned on may be manually set by the user or may be automatically set by the controller 40.

In Step S28, the controller 40 controls the light of one or more light emitting units 363 (light sources) for background illumination which are turned on. As described above, the light emitting units 363 are arranged in the movable direction of the illumination system 32 as viewed from the subject's eye E. The controller 40 has the light control function of controlling the light from the light emitting units 363 to reduce variation in the amount of the second illumination light L2 that reaches the subject's eye E from the light emitting units 363 regardless of the position of the illumination system 32. The controller 40 controls the outputs of the light emitting units 363 so that about the same amount of light is applied to the eye, whether one of the light emitting units 363 (the right light emitting unit 363 in FIG. 4) that is not hidden by the illumination system 32 as in the ophthalmologic apparatus 10A-2 of FIG. 4 is turned on to emit the second illumination light L2 or both of the light emitting units 363 that are not hidden by the illumination system 32 as in the ophthalmologic apparatus 10A-1 are turned on to emit the second illumination light L2. In other words, the controller 40 reduces the output of the second illumination light L2 when turning on the larger number of light emitting units 363 and increases the output of the second illumination light L2 when turning on the smaller number of light emitting units 363. As described above, the controller 40 controls the amount of the second illumination light L2 depending on the number of light sources emitting the second illumination light L2 that can reach the subject's eye E. Thus, when the examiner's observation or the image capturing in Step S29 is performed, variation in brightness of light around the observation region can be reduced regardless of the position of the illumination system 32.

Also in the present embodiment, for the observation of the subject's eye E, the illumination system 32 mainly irradiates the subject's eye E with the first illumination light L1 from a position deviated (separated) from the observation axis LA connecting the subject's eye E and the objective lens 50, which is the light receiving section of the observation system 34, in a direction inclined with respect to the observation axis LA. Thus, when the illumination system 32 is shifted leftward (or rightward) from the observation axis LA and the second illumination light L2 emitted from one of the light-emitting units 363 is blocked as in the ophthalmologic apparatus 10A-2 of FIG. 4, the one of the light emitting units 363 that cannot irradiate the subject's eye E with the second illumination light L2 is turned off. This can keep the ophthalmologic apparatus 10 from wasting power.

As described above, the ophthalmologic apparatus 10D of the second embodiment is configured to control the light emitting units 363 to reduce variation of the amount of the second illumination light L2 reaching the subject's eye E from the light emitting units 363 regardless of the position of the illumination system 32. This configuration can keep the subject's eye E from being shaded by the eyelid during the observation of the subject's eye E and can achieve more accurate observation of the subject's eye E with the background illumination by simple operation.

First Variation of Second Embodiment

The ophthalmologic apparatus 10D may be an ophthalmologic apparatus 10E including a magnetic encoder 62 instead of the optical encoder 61. The magnetic encoder 62 includes, for example, a magnetic sensor 621 (e.g., a Hall element) fixed to the rotation shaft 30 and a magnetic drum 622 which is a permanent magnet arranged in an annular shape around the rotation shaft 26. The magnetic encoder 62 outputs a detection signal corresponding to the rotation angle of the rotation shaft 30 with respect to the rotation shaft 26. The controller 40 can determine the rotation angle (relative position) of the illumination system 32 with respect to the observation system 34 based on the detection signal acquired from the magnetic encoder 62. The ophthalmologic apparatus 10E can be operated according to the flowchart of FIG. 10 in the same manner as the ophthalmologic apparatus 10D.

In addition to the optical encoder 61 and the magnetic encoder 62, the ophthalmologic apparatus 10 may use another encoder, such as a mechanical encoder (potentiometer) or an electromagnetic induction encoder, as a device for detecting the angle of the illumination system 32 with respect to the observation system 34.

Second and Third Variations of Second Embodiment

Figure 11:
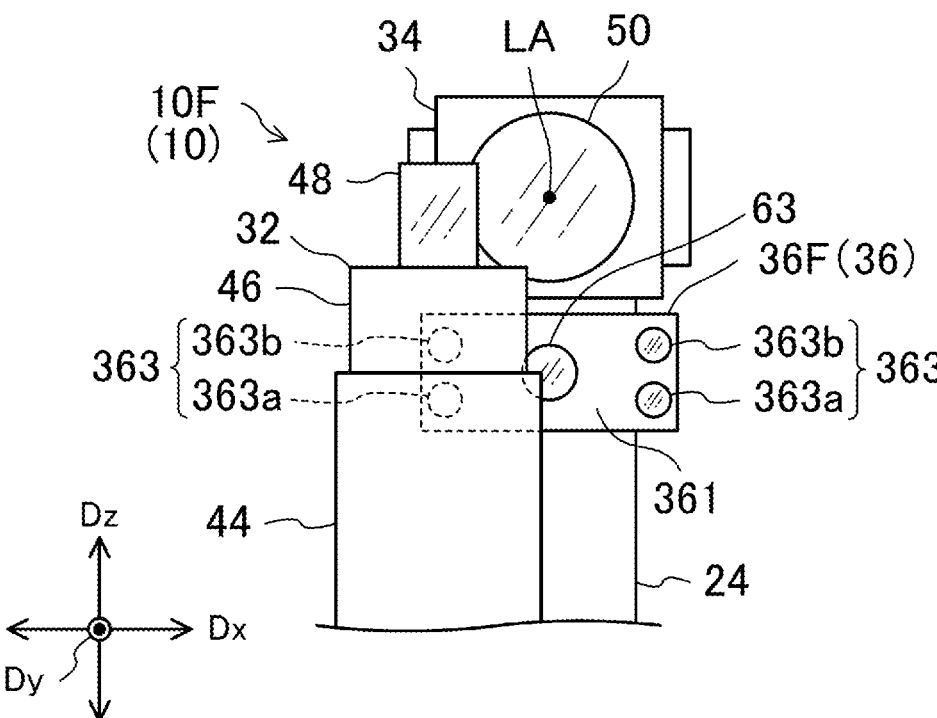
FIG. 11 is a front view illustrating ophthalmologic apparatuses of second and third variations of the second embodiment.
Figure 11:
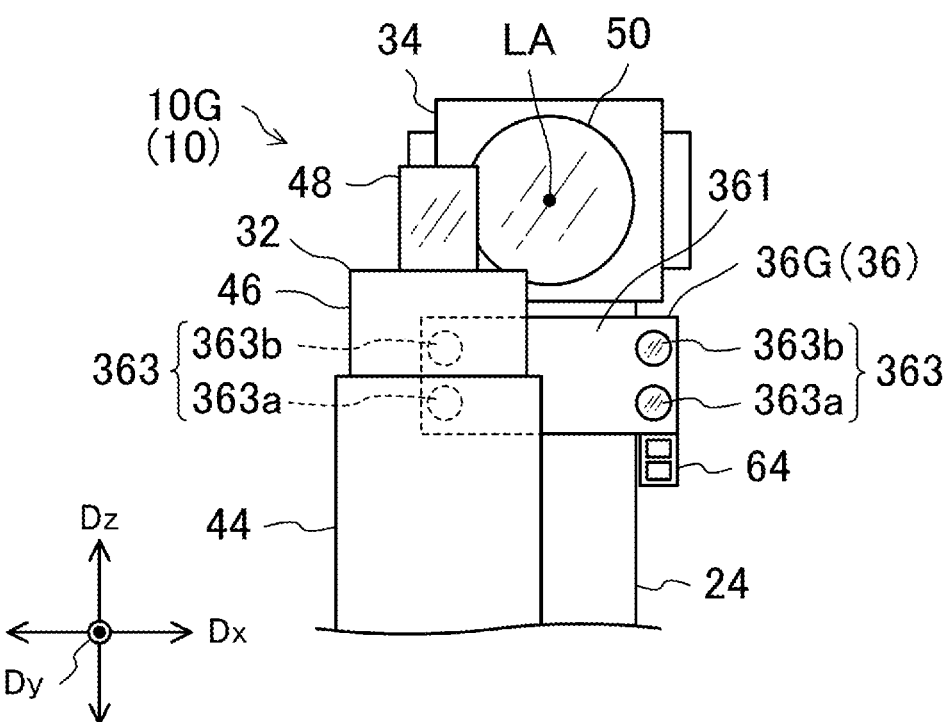

Second and third variations of the second embodiment will be described below. FIG. 11 is a front view illustrating an ophthalmologic apparatus 10F (10) of the second variation of the second embodiment and an ophthalmologic apparatus 10G (10) of the third variation of the second embodiment. In the description of the ophthalmologic apparatuses 10F and 10G, the same components as those of the ophthalmologic apparatus 10A are denoted by the same reference characters and will not be described or will be described simply.

An illuminator 36F of the ophthalmologic apparatus 10F includes a camera unit 63 substantially at the center of an illuminator body 361 in the left-right direction Dx. The ophthalmologic apparatus 10F can take an image of the illumination system 32 by the camera unit 63 to detect the position of the illumination system 32 from the acquired image by the controller 40. The illuminator 36F has correspondence information in which the rotation angles of the illumination system 32 and the observation system 34 are associated with light block information indicating how much the second illumination light L2 emitted from each light emitting unit 363 reaches the subject's eye E. The correspondence information is stored in advance in the storage. Alternatively, the storage stores predetermined angles of the rotation angles as threshold information for turning on or off the light emitting units 363.

The controller 40 of the ophthalmologic apparatus 10F can determine the rotation angle (relative position) of the illumination system 32 with respect to the observation system 34 based on the image acquired by the camera unit 63. The ophthalmologic apparatus 10F can be operated according to the flowchart of FIG. 10 in the same manner as the ophthalmologic apparatus 10D.

An illuminator 36G of the ophthalmologic apparatus 10G includes a time-of-flight (TOF) sensor 64 arranged substantially at the center of the illuminator body 361 in the left-right direction Dx. The ophthalmologic apparatus 10G can detect the presence or absence of the illumination system 32 by the TOF sensor 64. The illuminator 36G may also have correspondence information in which the rotation angles of the illumination system 32 and the observation system 34 are associated with light block information indicating how much the second illumination light L2 emitted from each light emitting unit 363 reaches the subject's eye E. The correspondence information is stored in advance in the storage. Alternatively, the storage may store predetermined angles of the above rotation angles as threshold information for turning on or off the light emitting units 363.

The controller 40 of the ophthalmologic apparatus 10G can determine the rotation angle (relative position) of the illumination system 32 with respect to the observation system 34 based on data about the position information of the illumination system 32 acquired from the TOF sensor 64. The ophthalmologic apparatus 10G can be operated according to the flowchart of FIG. 10 in the same manner as the ophthalmologic apparatus 10D.

Third Embodiment

Figure 12:
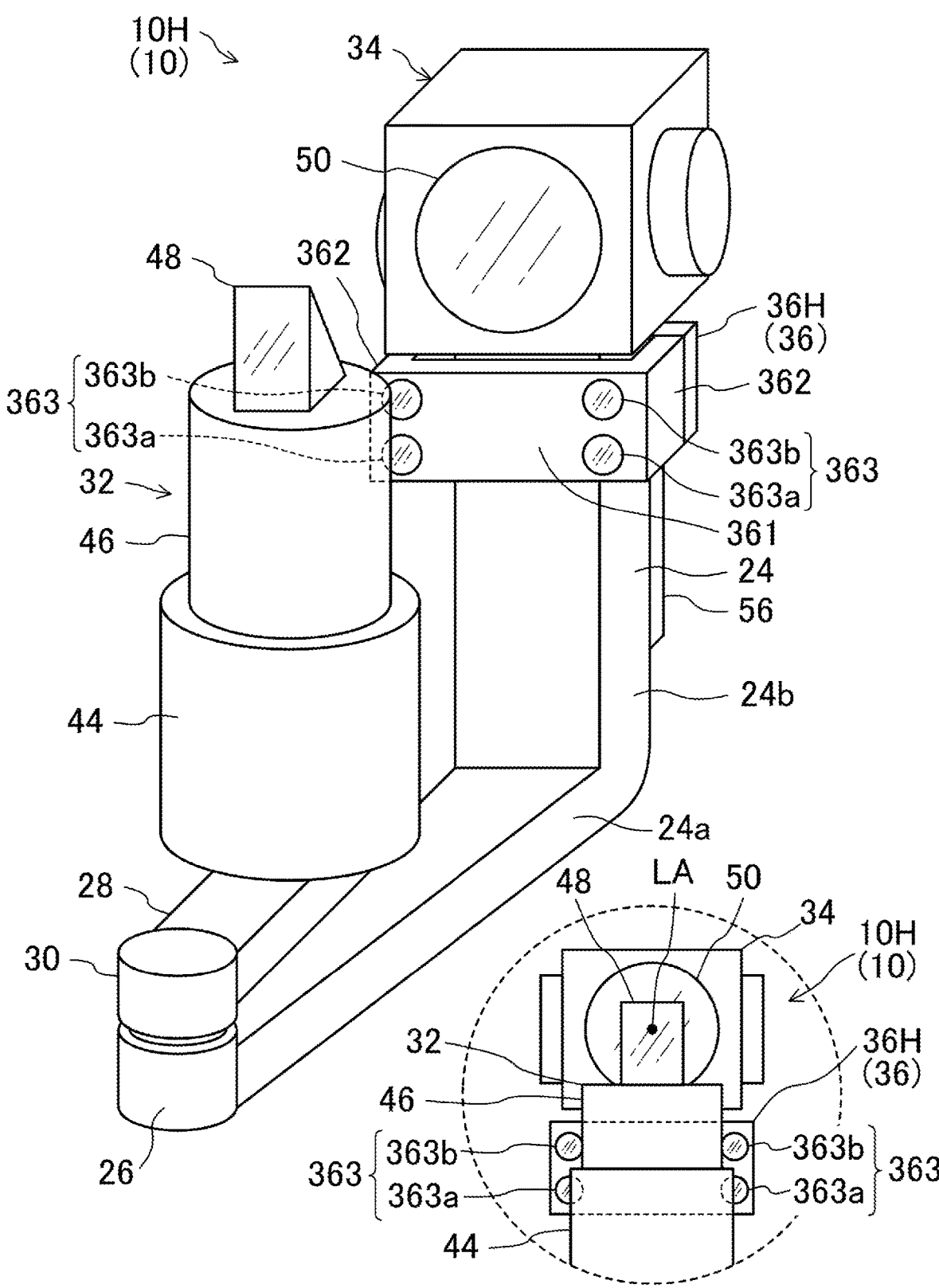
FIG. 12 is a perspective view of an illumination system and observation system of an ophthalmologic apparatus of a third embodiment as viewed from the subject.

A third embodiment will be described below. FIG. 12 is a perspective view of an illumination system 32 and observation system 34 of an ophthalmologic apparatus 10H (10) of the present embodiment as viewed from the subject's eye E. In the description of the ophthalmologic apparatus 10H, the same components as those of the ophthalmologic apparatus 10A are denoted by the same reference characters and will not be described or will be described simply.

The ophthalmologic apparatus 10H includes an illuminator 36H instead of the illuminator 36A of the ophthalmologic apparatus 10A. Compared with the illuminator 36A, the illuminator 36H has the thinner illuminator body 361 in the left-right direction and the narrower interval between the arms 362. In the ophthalmologic apparatus 10H using the slit light, for the observation of the subject's eye E, the illumination system 32 mainly irradiates the subject's eye E with the first illumination light L1 from a position deviated (separated) from the observation axis LA connecting the subject's eye E and the objective lens 50, which is the light receiving section of the observation system 34, and in a direction inclined with respect to the observation axis LA. Thus, even if the light emitting units 363 are arranged at positions where part (or all) of the light emitted from the light emitting units 363 is blocked by the illumination system 32 located substantially on the observation axis LA as in a front view shown in FIG. 12 illustrating the observation axis LA and its peripheral components, the illuminator 36H causes the controller 40 to detect the position of the illumination system 32 at which the second illumination light L2 is blocked by the illumination system 32, thereby making it possible to control the light from the light emitting units 363 depending on the relative position between the illumination system 32 and the light emitting units 363 and avoid the second illumination light L2 from being blocked during the observation of the subject's eye E. This can keep the subject's eye E from being shaded by the eyelid during the observation of the subject's eye E, allowing more accurate observation of the subject's eye E with the background illumination as in the first or second embodiment. The illuminator 36H that is thinned in the left-right direction can downsize the ophthalmologic apparatus 10H as a whole.

Further, the ophthalmologic apparatus 10H can perform the processes and operations of the flowchart of FIG. 10. This can keep the subject's eye E from being shaded by the eyelid during the observation of the subject's eye E, can achieve more accurate observation of the subject's eye E with the background illumination in fewer steps, and can downsize mainly the illuminator 36H and its peripheral components.

The ophthalmologic apparatus 10H may perform the processes and operations of the flowchart of FIG. 7. This can keep the subject's eye E from being shaded by the eyelid during the observation of the subject's eye E and can downsize the illuminator 36H.

First Variation of Third Embodiment

Figure 13:
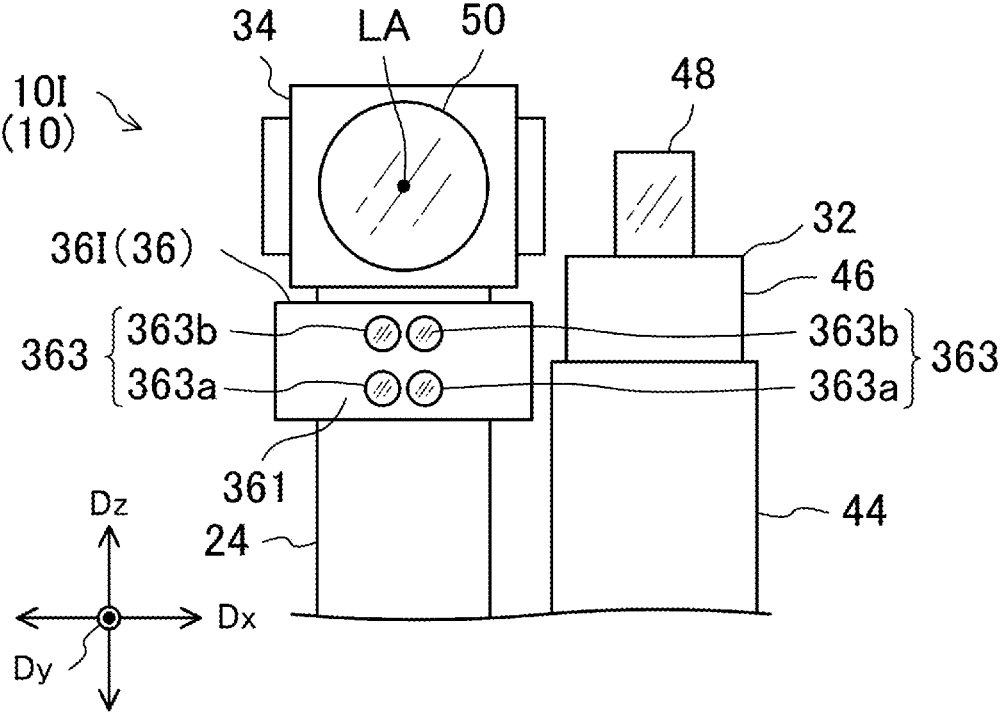
FIG. 13 is a front view illustrating an ophthalmologic apparatus of a first variation of the third embodiment.

A first variation of the third embodiment will be described below. FIG. 13 is a front view illustrating an ophthalmologic apparatus 10I (10) of a first variation of the third embodiment. The ophthalmologic apparatus 10I includes an illuminator 36I instead of the illuminator 36A of the ophthalmologic apparatus 10A. In the description of the ophthalmologic apparatus 10I, the same components as those of the ophthalmologic apparatus 10A are denoted by the same reference characters and will not be described or will be described simply.

The illuminator 36I of the ophthalmologic apparatus 10I includes a plurality of light emitting units 363 arranged substantially at the center of the illuminator body 361 in the left-right direction Dx.

The rotation angle of the illumination system 32 of the ophthalmologic apparatus 10I can be checked by the controller 40 using any component such as the encoder (e.g., the optical encoder 61 or the magnetic encoder 62), the camera unit 63, and the TOF sensor 64 which are described above. For the observation of the subject's eye E, the illumination system 321 mainly irradiates the subject's eye E with the first illumination light L1 from a position deviated (separated) from the observation axis LA connecting the subject's eye E and the objective lens 50, which is the light receiving section of the observation system 34, and in a direction inclined with respect to the observation axis LA. Thus, even if the light emitting units 363 are arranged at such intervals that cause the blocking of part or all of the second illumination light L2 emitted from each of the left and right light emitting units 363 arranged at the center of the illuminator body 361, the ophthalmologic apparatus 10I has substantially no influence on the accuracy of observation of the subject's eye E, thereby making it possible to avoid the subject's eye E from being shaded by the eyelid during the observation of the subject's eye E and allowing more accurate observation of the subject's eye E with the background illumination as in the first or second embodiment.

The ophthalmologic apparatus 10I can also perform the processes and operations of the flowchart of FIG. 10. This can keep the subject's eye E from being shaded by the eyelid during the observation of the subject's eye E, can achieve more accurate observation of the subject's eye E with the background illumination in fewer steps, and can downsize mainly the illuminator 36I and its peripheral components.

The ophthalmologic apparatus 10I may perform the processes and operations of the flowchart of FIG. 7. This can keep the subject's eye E from being shaded by the eyelid during the observation of the subject's eye E and can downsize the illuminator 36I.

Fourth Embodiment

Figure 14:
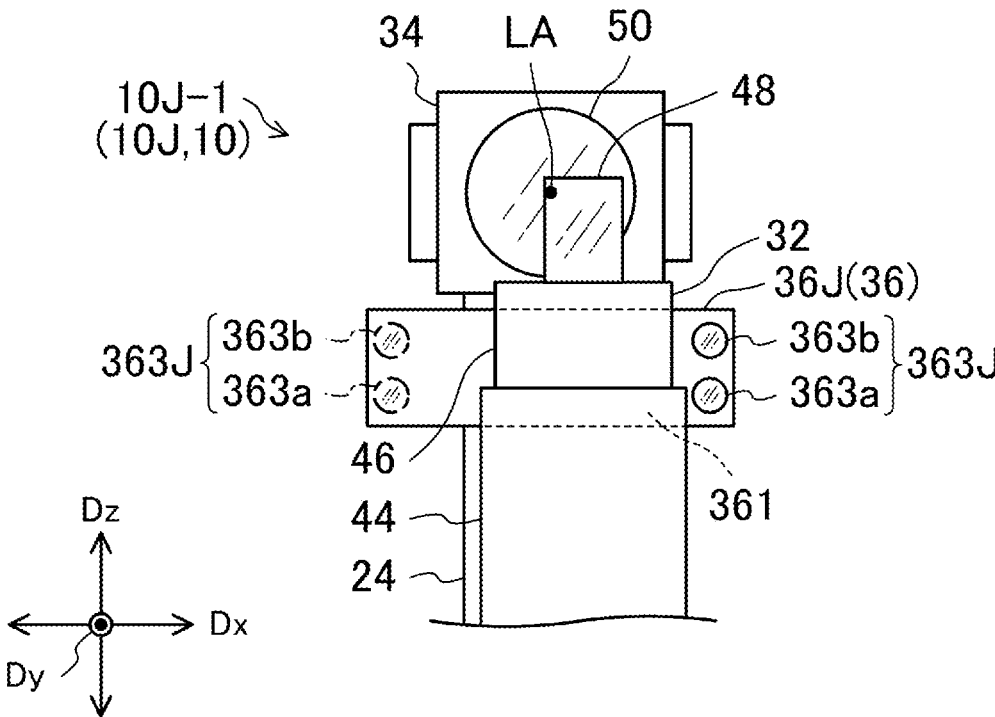
FIG. 14 is a front view of an ophthalmologic apparatus of a fourth embodiment.
Figure 14:
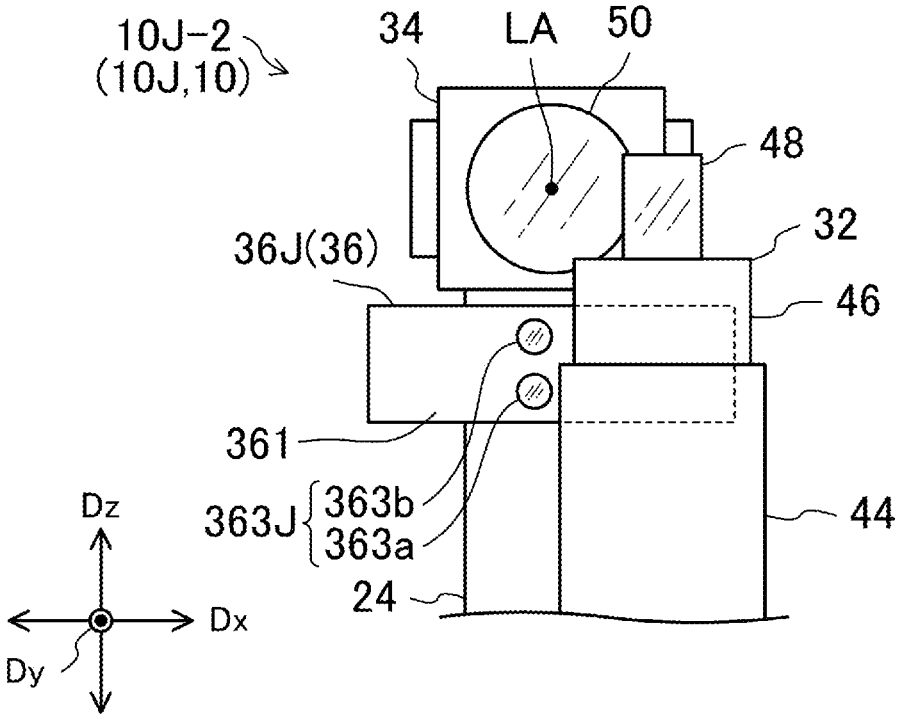
Figure 15:
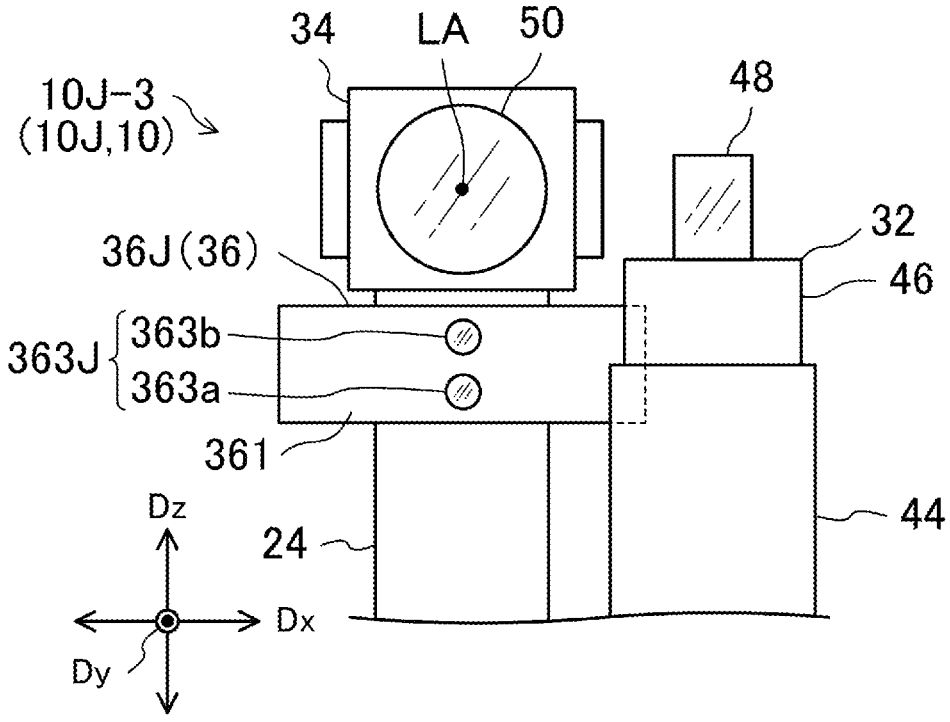
FIG. 15 is a front view of the ophthalmologic apparatus of the fourth embodiment.

A fourth embodiment of the present disclosure will be described below. FIGS. 14 and 15 are front views illustrating ophthalmologic apparatuses 10J (10J-1, 10J-2, and 10J-3) of the fourth embodiment. In the description of the ophthalmologic apparatuses 10J, the same components as those of the ophthalmologic apparatus 10A are denoted by the same reference characters and will not be described or will be described simply. Each ophthalmologic apparatus 10J is configured in the same manner as the ophthalmologic apparatus 10A except that the illuminator 36A is replaced with an illuminator 36J. The illuminator 36J includes a light emitting unit 363J that is movable in the left-right direction Dx which is a movable direction of the illumination system 32 as viewed from the subject's eye E. The ophthalmologic apparatus 10J includes the light emitting unit 363J on the front side (the side facing the subject's eye E) of the illuminator body 361. The light emitting unit 363J may be disposed, for example, in a power transmission mechanism using a rack gear and a pinion gear so as to be movable in the left-right direction Dx. However, any other power transmission mechanism may be applied.

The ophthalmologic apparatus 10J has an avoidance function of avoiding the second illumination light L2 emitted from the light emitting unit 363 from being blocked by the illumination system 32 by moving the light emitting unit 363 depending on the position of the illumination system 32. The avoidance function is performed under the control of the controller 40. As in the ophthalmologic apparatus 10J-1, when the illumination system 32 is located substantially at the center in the left-right direction Dx of the ophthalmologic apparatus 10J, the controller 40 positions (moves) the light emitting unit 363J on the right or left (indicated by the dash-dot line) of the illumination system 32.

As in the ophthalmologic apparatus 10J-2, when the illumination system 32 is located outward and away from the center of the ophthalmologic apparatus 10J in the left-right direction Dx, the controller 40 can move the light emitting unit 363J (e.g., one of the light emitting units 363J of the illuminator 36J) inward from the right (or left) part of the ophthalmologic apparatus 10J-2 in the left-right direction Dx to avoid the second illumination light L2 from being blocked by the illumination system 32. When viewed from the subject's eye E, the light emitting unit 363J may be moved to the left when the illumination system 32 is moved to the right or may be moved to the right when the illumination system 32 is moved to the left.

As in the ophthalmologic apparatus 10J-3, when the illumination system 32 is located outward and away from the center of the ophthalmologic apparatus 10J in the left-right direction Dx, the controller 40 may move the light emitting unit 363J to the substantial center of the ophthalmologic apparatus 10J-3 in the left-right direction Dx to avoid the second illumination light L2 from being blocked by the illumination system 32.

In the ophthalmologic apparatus 10J of the fourth embodiment, the light emitting unit 363J is configured to be movable. This configuration can avoid the subject's eye E from being shaded by the eyelid and can avoid the second illumination light L2 as the background illumination light from being blocked by the illumination system 32, allowing accurate observation of the subject's eye E. The ophthalmologic apparatus 10J can provide the ophthalmologic apparatus 10J (a slit lamp microscope) that can avoid flare and allows accurate observation of the subject's eye E.

The light emitting unit 363J of the ophthalmologic apparatus 10J may be a plurality of light emitting units 363J arranged on the left and right parts of the illuminator body 361 of the illuminator 36J. In this case, when the illumination system 32 is located outward and away from the center of the ophthalmologic apparatus 10J in the left-right direction Dx, all the light emitting units 363J may be moved to the center position as viewed from the subject's eye E, or both of the light emitting units 363J may be moved to the left when the illumination system 32 is moved to the right or may be moved to the right when the illumination system 32 is moved to the left as viewed from the subject's eye E.

Although not shown, the controller 40 may move one or both of the light emitting units 363J arranged on the left and right parts of the illuminator body 361 in the same direction as the movement direction of the illumination system 32 to avoid the second illumination light L2 from being blocked by the illumination system 32. The controller 40 may move the light emitting units 363J rightward or leftward with the right and left light emitting units 363J kept located on the right and left parts of the illumination system 32 when viewed from the subject's eye E.

The configuration of the ophthalmologic apparatus 10J including the movable light emitting unit 363J may be applied to the other ophthalmologic apparatuses 10A to 10I.

The ophthalmologic apparatus 10J is not limited to a control example in which the infrared light source 363a and the visible light source 363b included in the light emitting unit 363J are simultaneously moved, and the light sources may be individually moved.

The ophthalmologic apparatus 10 and the method for controlling the light source of the ophthalmologic apparatus 10 have been described above. The ophthalmologic apparatus 10 includes: the illumination system 32 that is supported to be rotatable about the subject's eye E with the irradiation direction of the first illumination light L1 kept toward the subject's eye E; the observation system 34 that is arranged opposite to the position of the subject's eye E across the illumination system 32; and the light emitting unit 363 for background illumination that is provided in the observation system 34 and located below the subject's eye E. The light from the light emitting unit 363 is controlled depending on the relative position between the illumination system 32 and the light emitting unit 363. Thus, the ophthalmologic apparatus 10 that allows more accurate observation of the subject's eye E with the background illumination can be provided.

It has also been described above an example of the ophthalmologic apparatus 10 including the illumination system 32 that is supported to be rotatable about the subject's eye E with the irradiation direction of the first illumination light L1 kept toward the subject's eye E and the observation system 34 that has the camera device 56 and is arranged opposite to the position of the subject's eye E across the illumination system 32. The camera device 56 includes the imaging unit 561 that receives reflection of the first illumination light L1 from the subject's eye E and the light emitting unit 363 for background illumination provided in the observation system 34 and located below the subject's eye E. This configuration can provide the ophthalmologic apparatus 10 and the camera device 56 which have the background illumination function and the imaging function for the subject's eye E in a simple configuration.

An example of the ophthalmologic apparatus 10 has also been described above, which includes: the illumination system 32 that is supported to be rotatable about the subject's eye E with the irradiation direction of the first illumination light L1 kept toward the subject's eye E; the observation system 34 arranged opposite to the position of the subject's eye E across the illumination system 32; and the light emitting unit 363 for background illumination provided in the observation system 34 and located below the subject's eye E. The light emitting unit 363 includes a plurality of light emitting units 363 arranged in the movable direction of the illumination system 32 as viewed from the subject's eye E. This can provide the ophthalmologic apparatus 10 that can avoid the second illumination light L2 as the background illumination light of the illumination system 32 from being blocked, can keep the subject's eye E from being shaded by the eyelid, and can achieve more accurate observation of the subject's eye E.

An example of the ophthalmologic apparatus 10 has also been described above, which includes: the illumination system 32 that is supported to be rotatable about the subject's eye E with the irradiation direction of the first illumination light L1 kept toward the subject's eye E; the observation system 34 arranged opposite to the position of the subject's eye E across the illumination system 32; and the light emitting unit 363 for background illumination provided in the observation system 34 and located below the subject's eye E. The ophthalmologic apparatus 10 has the avoidance function of avoiding the second illumination light L2 emitted from the light emitting unit 363 from being blocked by the illumination system 32 by moving the light emitting unit 363 depending on the position of the illumination system 32. This can provide the ophthalmologic apparatus 10 and a method of controlling the illumination of the ophthalmologic apparatus 10 that can avoid the second illumination light L2 as the background illumination light of the illumination system 32 from being blocked, can keep the subject's eye E from being shaded by the eyelid, and can achieve more accurate observation of the subject's eye E.

Although the embodiments of the present disclosure have been described above, the aspects of the present disclosure are not limited to the configurations in the embodiments.

The invention claimed is:

1. An ophthalmologic apparatus, comprising:

an illumination system that is supported to be rotatable about a subject's eye with an irradiation direction of illumination light kept toward the subject's eye;

an observation system that has a camera device and is arranged opposite to a position of the subject's eye across the illumination system, the camera device including an imaging unit that receives reflection of the illumination light from the subject's eye and a light emitting unit for background illumination that is provided in the observation system and located below the subject's eye, the camera device arranged opposite to the subject's eye in the observation system; and an illuminator having the light emitting unit for background illumination connected to the camera device by sandwiching a vertical arm portion of the observation system between arms of a U-shaped illuminator body, the illuminator receiving power from a power supply circuit of the camera device through an inside of at least one of the arms of the U-shaped illuminator body.

2. The ophthalmologic apparatus of claim 1, wherein the illuminator is configured to be removably inserted in the camera device from a side of the subject's eye, the camera device being wider than the vertical arm portion in a movable direction of the illumination system when viewed from the side of the subject's eye.

3. The ophthalmologic apparatus of claim 1, wherein the light emitting unit includes a control circuit, the control circuit being housed in the camera device.

4. The ophthalmologic apparatus of claim 1, wherein the light emitting units are arranged in a movable direction of the illumination system as viewed from the subject's eye.

5. The ophthalmologic apparatus of claim 4, wherein the ophthalmologic apparatus has a light control function controlling the light emitted from the light emitting units depending on a relative position between the illumination system and the light emitting units.

6. The ophthalmologic apparatus of claim 5, wherein viewing in plan in a direction of a rotation shaft of the illumination system, the light emitting units are arranged on the outside of an angular range of a light-blocking angle that is formed between two tangents to the illumination system located on the observation axis connecting a light receiving section of the observation system and an origin which is the position of the subject's eye.

7. The ophthalmologic apparatus of claim 4, wherein the illumination system includes a slit lamp that emits illumination light and a deflection unit that deflects the illumination light to the subject's eye, and for the observation of the subject's eye, the illumination system applies the illumination light to the subject's eye from a position deviated from the observation axis connecting the subject's eye and the light receiving section of the observation system.

8. The ophthalmologic apparatus of claim 4, wherein the illumination system includes a slit lamp that emits illumination light and a deflection unit that deflects the illumination light to the subject's eye, and for the observation of the subject's eye, the illumination system applies the illumination light to the subject's eye from a position deviated from the observation axis connecting the subject's eye and the light receiving section of the observation system.

9. The ophthalmologic apparatus of claim 1, wherein the light emitting units has the function of automatically selecting and turning on one of the light emitting units whose light is not blocked by the illumination system and turning off the other light emitting unit whose light is blocked by the illumination system.

10. The ophthalmologic apparatus of claim 9, wherein the light emitting units are arranged in a movable direction of the illumination system as viewed from the subject's eye, and the ophthalmologic apparatus has a light control function of controlling the light from the light emitting units to reduce variation in the amount of the second illumination light that reaches the subject's eye from the light emitting units regardless of the position of the illumination system.

11. The ophthalmologic apparatus of claim 1, wherein the ophthalmologic apparatus has an avoidance function of avoiding second illumination light emitted from the light emitting unit from being blocked by the illumination system by moving the light emitting unit depending on the position of the illumination system.

12. The ophthalmologic apparatus of claim 11, wherein the light emitting units are arranged in a movable direction of the illumination system as viewed from the subject's eye, the light emitting unit is movable in the movable direction of the illumination system.

13. The ophthalmologic apparatus of claim 12, wherein all the light emitting units may be moved to the center position as viewed from the subject's eye.

14. The ophthalmologic apparatus of claim 13, wherein one or both of the light emitting units may be moved rightward or leftward with the right and left light emitting units in the same direction as a movement direction of the illumination system kept located on the right and left parts of the illumination system when viewed from the subject's eye.

15. A method of controlling illumination of an ophthalmologic apparatus, the ophthalmologic apparatus comprising an illumination system that is supported to be rotatable about a subject's eye with an irradiation direction of a first illumination light kept toward the subject's eye, an observation system arranged opposite to a position of the subject's eye across the illumination system, and a light emitting unit for background illumination provided in the observation system and located below the subject's eye, the method comprising:

controlling the light from the light emitting unit depending on a relative position between the illumination system and the light emitting unit.

16. A method of controlling the illumination of an ophthalmologic apparatus of claim 15, wherein the method includes avoiding second illumination light emitted from the light emitting unit from being blocked by the illumination system by moving the light emitting unit depending on the position of the illumination system.

* * * * *